US010555998B2

(12) United States Patent
Qiao et al.

(10) Patent No.: US 10,555,998 B2
(45) Date of Patent: Feb. 11, 2020

(54) INACTIVATED EQUINE INFLUENZA VIRUS VACCINES

(71) Applicant: Intervet Inc., Madison, NJ (US)

(72) Inventors: Zhisong Qiao, Omaha, NE (US); Catherine M. Peters, Osage, IA (US); Zhuyan Guo, Scotch Plains, NJ (US); Wendy Vaala, Alma, WI (US); Craig Barnett, Paola, KS (US)

(73) Assignee: Intervet Inc., Madison, NJ (US)

( * ) Notice: Subject to any disclaimer, the term of this patent is extended or adjusted under 35 U.S.C. 154(b) by 256 days.

(21) Appl. No.: 15/528,549

(22) PCT Filed: Nov. 23, 2015

(86) PCT No.: PCT/EP2015/077323
§ 371 (c)(1),
(2) Date: May 22, 2017

(87) PCT Pub. No.: WO2016/083287
PCT Pub. Date: Jun. 2, 2016

(65) Prior Publication Data
US 2017/0252428 A1    Sep. 7, 2017

Related U.S. Application Data

(60) Provisional application No. 62/083,542, filed on Nov. 24, 2014, provisional application No. 62/102,817, filed on Jan. 13, 2015.

(51) Int. Cl.
*A61K 39/145* (2006.01)
*C12N 7/00* (2006.01)
*C07K 14/005* (2006.01)
*A61K 39/00* (2006.01)

(52) U.S. Cl.
CPC .......... *A61K 39/145* (2013.01); *C07K 14/005* (2013.01); *C12N 7/00* (2013.01); *A61K 2039/5252* (2013.01); *A61K 2039/552* (2013.01); *A61K 2039/70* (2013.01); *C12N 2760/16121* (2013.01); *C12N 2760/16134* (2013.01); *C12N 2760/16163* (2013.01)

(58) Field of Classification Search
None
See application file for complete search history.

(56) References Cited

U.S. PATENT DOCUMENTS

| 6,177,082 | B1 | 1/2001 | Dowling et al. |
| 7,384,642 | B2 | 6/2008 | Minke et al. |
| 7,572,620 | B2 | 8/2009 | Olsen et al. |
| 7,722,884 | B2 | 5/2010 | Shields et al. |
| 7,959,929 | B2 * | 6/2011 | Crawford ............ A61K 39/145 424/206.1 |
| 9,393,298 | B2 | 7/2016 | Buchanan et al. |
| 9,480,739 | B2 | 11/2016 | Eddy et al. |
| 2006/0153871 | A1 | 7/2006 | Olsen |

FOREIGN PATENT DOCUMENTS

| WO | 1993015763 A1 | 9/1993 |
| WO | 1994017826 A1 | 8/1994 |
| WO | 2000009702 A1 | 2/2000 |
| WO | 2001060849 A2 | 8/2001 |
| WO | 2007047728 A2 | 4/2007 |
| WO | 2007047938 A2 | 4/2007 |
| WO | 2007118206 A2 | 10/2007 |
| WO | 2008097970 A2 | 8/2008 |
| WO | 2009097291 A2 | 8/2009 |
| WO | 2012125525 A2 | 9/2012 |
| WO | 2016210083 A2 | 12/2016 |

OTHER PUBLICATIONS

Antanasijevic et al., The Journal of Biological Chemistry vol. 289, No. 32, pp. 22237-22245 (Year: 2014).*
Barbey-Martin, C et al., An antibody that prevents the hemagglutinin low pH fusogenicc transition, Virology, 2002, pp. 70-74, 294.
Collins, PJ et al, Recent evolution of equine influenza and the origin of canine influenza, Proceedings of the national acadamy of sciences, Jul. 14, 2014, pp. 11175, vol. 111 No. 30.
Crawford, et al., Transmission of Equine Influenca Virus to Dogs, Science, 2005, 482-485, 310, US.
Daly, JM et al., Antigenic and genetic evolution of equine H3N8 influenza A viruses, Journal of General Virology, 1996, pp. 661-671, 66.
Ekiert, DC et al., A highly conserved neutralizing epitope on group 2 influenza A viruses, Science, 2011, pp. 843-850, 333.
Fleury, D et al., A complex of influenza hemagglutinin with a neutralizing antibody that binds outside the virus receptor binding site, Nature Structural Biology, 2014, pp. 530-534, 6(6).
Fleury, D et al., Structural evidence for recognition of a single epitope by two distinct antibodies, Proteins: Structure, Function and Genetics, 2000, pp. 572-578, 40.
Hayward, JJ et al, Microevolution of Canine Influenza Virus in Shelters and Its Molecular Epidemiology in the United States, Journal of Virology, Oct. 13, 2010, pp. 12636-12645, vol. 84, No. 24.
International Search Report for—PCTEP2015077323 dated Mar. 2, 2016, 6 pages.
Lai, Ack et al., Alternate circulation of recent equine-2 influenza viruses (H3N8) from two distinct lineages in the United States, Virus Research, 2004, pp. 159-164, 100.

(Continued)

*Primary Examiner* — Shanon A. Foley
*Assistant Examiner* — Myron G Hill

(57) ABSTRACT

The present invention relates to equine influenza virus (EIV) isolates that when administered in vaccines to equine provide protection against currently emerging EIV strains in the U.S. The present invention also relates to inactivated EIV isolates. In addition, the present invention also relates to safe and efficacious vaccines that comprise the EIV isolates, as well as to corresponding subunit vaccines. The present invention further relates to methods of administering such safe and efficacious vaccines to equine.

20 Claims, 7 Drawing Sheets
Specification includes a Sequence Listing.

(56) References Cited

OTHER PUBLICATIONS

Lewis, NS et al., Antigenic and Genetic Evolution of Equine Influenza A (H3N8) Virus from 1968 to 2007, Journal of Virology, 2011, pp. 12742-12749, 85(23).
Myers, C et al., Equine Influenza Virus, Clinical Techniques in Equine Practice, 2006, pp. 187-196, 5(3).
Payungporn, S et al., Influenza A virus (H3N8) in dogs with respiratory disease, Florida, Emerging Infectious Diseases, 2008, pp. 902-908, 14(6).
Pecoraro, Heidi L, et al, Evolution of the hemagglutinin gene of H3N8 canine influenza virus in dogs, Virus Genes, Jul. 24, 2014, pp. 393-399, vol. 49, No. 3.
Peek, SF et al., Acute respiratory distress syndrome and fatal interstitial pneumonia associated with equine influenza in a neonatal foal, Journal of veterinary internal medicine, 2004, pp. 132-134, 18.
Pusterla et al., Voluntary Surveillance Program for Equine Influenza Virus in the United States from 2010 to 2013, J Vet Intern Med, 2015, pp. 1-6,-, Wiley Periodicals, Inc.
Rivailler P et al, Evolution of canine an equine influenza (H#N*) virusses co-circulating between 2005 and 2008, Virology, Dec. 5, 2010, pp. 71, vol. 408, No. 1, Elsevier, Amsterdam.
Skehel, J et al., Receptor binding and membrane fusion in virus entry: the influenza hemagglutinin, Annu. Rev. Biochem., 2000, pp. 531-569, 69.
Woodward, AL et al., Development of a surveillance scheme for equine influenza in the UK and characterisation of viruses isolated in Europe, Dubai and the USA from 2010-2013, Veterinary Microbiology, 2014, 113-127, 169.

\* cited by examiner

Figure 1: Alignment of HA protein sequence of EIV OH03 and FL13 isolate

```
1    M K T T I I L I L L L T H W A Y S Q N P I S G N N T A T L C L G H H A V A N G T L V K T I S D D Q    A.Eq.Ohio.2003
1    M K T T I I L I L L L T H W A Y S Q N P I S D N N T A T L C L G H H A A A N G T L V K T I S D D Q    A.Eq.Florida.2013

49   I E V T N A T E L V Q S I S M G K I C N N S Y R I L D G R N C T L I D A M L G D P H C D A F Q Y    A.Eq.Ohio.2003
49   I E V T N A T E L V Q S I S M G K I C N N S Y R I L D G K N C T L I D A M L G D P H C D A F Q Y    A.Eq.Florida.2013

97   E N W D L F I E R S S A F S N C Y P Y D I P D Y A S L R S I V A S S G T L E F T A E G F T W T G    A.Eq.Ohio.2003
97   E N W D L F I E R S S A F S N C Y P Y D I P N Y A S L R S I V A S S G T L E F T A E G F T W T G    A.Eq.Florida.2013

145  V T Q N G R S G A C K R G S A D S F F S R L N W L T K S G S S Y P T L N V T M P N N K N F D K L    A.Eq.Ohio.2003
145  V T Q N G R S G S C K R G S A D S F F S R L N W L T K S G S S Y P T L N V T M P N N K N F D K L    A.Eq.Florida.2013

193  Y I W G I H H P S S N Q E Q T K L Y I Q E S G R V T V S T K R S Q Q T I I P N I G S R P W V R G    A.Eq.Ohio.2003
193  Y I W G I H H P S S T Q E Q T K L Y I Q E S G R V T V S T K R S Q Q T I I P N I G S R P L I R G    A.Eq.Florida.2013

241  Q S G R I S I Y W T I V K P G D I L M I N S N G N L V A P R G Y F K L K T G K S S V M R S D V P    A.Eq.Ohio.2003
241  Q S G R I S I Y W T I V K P G D I L M I N S N G N L V A P R G Y F K L K T G K S S V M R S D V P    A.Eq.Florida.2013

289  I D I C V S E C I T P N G S I S N D K P F Q N V N K V T Y G K C P K Y I R Q N T L K L A T G M R    A.Eq.Ohio.2003
289  I D I C V S E C I T P N G S I S N D K P F Q N V N K V T Y G K C P K Y I R R N T L K L A T G M R    A.Eq.Florida.2013

337  N V P E K Q I R G I F G A I A G F I E N G W E G M V D G W Y G F R Y Q N S E G T G Q A A D L K S    A.Eq.Ohio.2003
337  N V P E K Q I R G I F G A I A G F I E N G W E G M V D G W Y G F R Y Q N S E G T G Q A A D L K S    A.Eq.Florida.2013

385  T Q A A I D Q I N G K L N R V I E R T N E K F H Q I E K E F S E V E G R I Q D L E K Y V E D T K    A.Eq.Ohio.2003
385  T Q A A I D Q I N G K L N R V I E R T N E K F H Q I E K E F S E V E G R I Q D L E K Y V E D T K    A.Eq.Florida.2013

433  I D L W S Y N A E L L V A L E N Q H T I D L T D A E M N K L F E K T R R Q L R E N A E D M G G G    A.Eq.Ohio.2003
433  I D L W S Y N A E L L V A L E N Q H T I D L T D A E M N K L F E K T R R Q L R E N A E D M G G G    A.Eq.Florida.2013

481  C F K I Y H K C D N A C I G S I R N G T Y D H Y I Y R D E A L N N R F Q I K G V E L K S G Y K D    A.Eq.Ohio.2003
481  C F K I Y H K C D N A C I G S I R N G T Y D H Y I Y R D E A L N N R F Q I K G V E L K S G Y K D    A.Eq.Florida.2013

529  W I L W I S F A I S C F L I C V V L L G F I M W A C Q K G N I R C N I C I                          A.Eq.Ohio.2003
529  W I L W I S F A I S C F L I C V V L L G                                                           A.Eq.Florida.2013
```

Figure 2: Alignment of mature HA protein of human influenza HK68, EIV OH03 and FL13 isolates

```
1    Q D L P G N D N S T A T L C L G H H A V P N G T L V K T I T D D Q I E    A.Human.HK.1968
1    S Q N P I S G N N T A T L C L G H H A V A N G T L V K T I S D D Q I E    A.Eq.Ohio.2003m
1    S Q N P I S D N N T A T L C L G H H A A A N G T L V K T I S D D Q I E    A.Eq.Florida.2013m 36   V T N A T E L V Q S S S T G K I C N N P H R I L D G I D C T L I D A L    A.Human.HK.1968
36   V T N A T E L V Q S I S M G K I C N N S Y R I L D G R N C T L I D A M    A.Eq.Ohio.2003m
36   V T N A T E L V Q S I S M G K I C N N S Y R I L D G K N C T L I D A M    A.Eq.Florida.2013m 71   L G D P H C D V F Q N E T W D L F V E R S K A F S N C Y P Y D V P D Y    A.Human.HK.1968
71   L G D P H C D A F Q Y E N W D L F I E R S S A F S N C Y P Y D I P D Y    A.Eq.Ohio.2003m
71   L G D P H C D A F Q Y E N W D L F I E R S S A F S N C Y P Y D I P N Y    A.Eq.Florida.2013m 106  A S L R S L V A S S G T L E F I T E G F T W T G V T Q N G G S N A C K    A.Human.HK.1968
106  A S L R S I V A S S G T L E F T A E G F T W T G V T Q N G R S G A C K    A.Eq.Ohio.2003m
106  A S L R S I V A S S G T L E F T A E G F T W T G V T Q N G R S G S C K    A.Eq.Florida.2013m 141  R G P G S D F F S R L N W L T K S G S T Y P V L N V T M P N N D N F D    A.Human.HK.1968
141  R G S A D S F F S R L N W L T K S G S S Y P T L N V T M P N N K N F D    A.Eq.Ohio.2003m
141  R G S A D S F F S R L N W L T K S G S S Y P T L N V T M P N N K N F D    A.Eq.Florida.2013m 176  K L Y I W G I H H P S T N Q E Q T S L Y V Q A S G R V T V S T R R S Q    A.Human.HK.1968
176  K L Y I W G I H H P S S N Q E Q T K L Y I Q E S G R V T V S T K R S Q    A.Eq.Ohio.2003m
176  K L Y I W G I H H P S S T Q E Q T K L Y I Q E S G R V T V S T K R S Q    A.Eq.Florida.2013m 211  Q T I I P N I G S R P W V R G L S S R I S I Y W T I V K P G D V L V I    A.Human.HK.1968
211  Q T I I P N I G S R P W V R G Q S G R I S I Y W T I V K P G D I L M I    A.Eq.Ohio.2003m
211  Q T I I P N I G S R P L I R G Q S G R I S I Y W T I V K P G D I L M I    A.Eq.Florida.2013m 246  N S N G N L I A P R G Y F K M R T G K S S I M R S D A P I D T C I S E    A.Human.HK.1968
246  N S N G N L V A P R G Y F K L K T G K S S V M R S D V P I D I C V S E    A.Eq.Ohio.2003m
246  N S N G N L V A P R G Y F K L K T G K S S V M R S D V P I D I C V S E    A.Eq.Florida.2013m 281  C I T P N G S I P N D K P F Q N V N K I T Y G A C P K Y V K Q N T L K    A.Human.HK.1968
281  C I T P N G S I S N D K P F Q N V N K V T Y G K C P K Y I R Q N T L K    A.Eq.Ohio.2003m
281  C I T P N G S I S N D K P F Q N V N K V T Y G K C P K Y I R R N T L K    A.Eq.Florida.2013m 316  L A T G M R N V P E K Q T R G L F G A I A G F I E N G W E G M I D G W    A.Human.HK.1968
316  L A T G M R N V P E K Q I R G I F G A I A G F I E N G W E G M V D G W    A.Eq.Ohio.2003m
316  L A T G M R N V P E K Q I R G I F G A I A G F I E N G W E G M V D G W    A.Eq.Florida.2013m 351  Y G F R H Q N S E G T G Q A A D L K S T Q A A I D Q I N G K L N R V I    A.Human.HK.1968
351  Y G F R Y Q N S E G T G Q A A D L K S T Q A A I D Q I N G K L N R V I    A.Eq.Ohio.2003m
351  Y G F R Y Q N S E G T G Q A A D L K S T Q A A I D Q I N G K L N R V I    A.Eq.Florida.2013m 386  E K T N E K F H Q I E K E F S E V E G R I Q D L E K Y V E D T K I D L    A.Human.HK.1968
386  E R T N E K F H Q I E K E F S E V E G R I Q D L E K Y V E D T K I D L    A.Eq.Ohio.2003m
386  E R T N E K F H Q I E K E F S E V E G R I Q D L E K Y V E D T K I D L    A.Eq.Florida.2013m 421  W S Y N A E L L V A L E N Q H T I D L T D S E M N K L F E K T R R Q L    A.Human.HK.1968
421  W S Y N A E L L V A L E N Q H T I D L T D A E M N K L F E K T R R Q L    A.Eq.Ohio.2003m
421  W S Y N A E L L V A L E N Q H T I D L T D A E M N K L F E K T R R Q L    A.Eq.Florida.2013m 456  R E N A E E M G N G C F K I Y H K C D N A C I E S I R N G T Y D H D V    A.Human.HK.1968
456  R E N A E D M G G G C F K I Y H K C D N A C I G S I R N G T Y D H Y I    A.Eq.Ohio.2003m
456  R E N A E D M G G G C F K I Y H K C D N A C I G S I R N G T Y D H Y I    A.Eq.Florida.2013m 491  Y R D E A L N N R F Q I K G                                              A.Human.HK.1968
491  Y R D E A L N N R F Q I K G                                              A.Eq.Ohio.2003m
491  Y R D E A L N N R F Q I K G                                              A.Eq.Florida.2013m
```

Figure 3: Model of HA protein of EIV FL13

Figure 4: Location of mutations and HA nAb epitopes mapping on FL13 HA

Figure 5: Location of R62K in HC45 epitope and its potential effects on antibody binding a) Residues of HC45 epitope on the HA surface. R62K is at the center of HC45 epitope b) Interactions of R62K with Tyr32 of HC45 nAb. Both arginine and lysine are capable of making cation-pi interactions with Tyr 32 of HC45. But lysine is not able to make the pi-pi interactions that the arginine can Figure 6: Location of N188T in HC63 epitope and its potential effects on antibody binding a) Residues in HC63 epitope and location of N188T (at the periphery of HC63 epitope).

b) Impact of N188T mutation on the HA association with HC63: N188 from HA(1) is involved in polar interactions with R201 and N246 of HA(2). For reference, the sidechain of T188 is also indicated (white stick).

Figure 7: Location of A138S, W222L and V223I and receptor binding site (RBS)

a) Residues (sticks) in the RBS region mapped onto the HA protein (surface). A138S is at the perimeter of RBS b) Close-up view of spatial arrangement of residues A138S, W222L, V223I, and RBS key residue Y98, as space-fill models.

INACTIVATED EQUINE INFLUENZA VIRUS VACCINES

CROSS-REFERENCE TO RELATED APPLICATIONS

This application is a national stage entry under 35 U.S.C. § 371 of PCT/EP2015/077323 filed on Nov. 23, 2015, which claims priority to U.S. Application No. 62/083,542 filed on Nov. 24, 2014 and U.S. Application No. 62/102,817 filed on Jan. 13, 2015. The content of PCT/EP2015/077323 is hereby incorporated by reference in its entirety.

FIELD OF THE INVENTION

The present invention pertains to equine influenza virus (EIV) isolates that when administered in vaccines to equine provide protection against currently emerging EIV strains. The present invention also pertains to inactivated EIV isolates. In addition, the present invention pertains to safe and efficacious vaccines that comprise the EIV isolates, as well as to related subunit vaccines. The present invention further pertains to methods of administering such safe and efficacious vaccines to equine.

BACKGROUND OF THE INVENTION

Respiratory disease in horses significantly impacts both the well-being of the infected animals, as well as their financial value to their owners. The major etiological agent for respiratory disease in horses is equine influenza virus (EIV), a type A influenza virus of the orthomyxovirus family.

Eight RNA segments contain the entire EIV genome. This genome encodes a matrix protein (MP) that surrounds the RNA segments, a nucleoprotein (NP) that coats the RNA segments, and a complex of polymerase enzymes that together with NP serves to transcribe and replicate the viruses within the nucleus of an infected cell. A lipid bilayer virion envelope encloses the entire viral structure. The EIV genome also encodes two main surface glycoproteins, hemagglutinin (HA) and neuraminidase (NA), that project out from the lipid bilayer. HA serves to attach the virus to the host cell, whereas NA acts on the mucus bonds within the respiratory mucus blanket to permit the virus access to the underlying epithelial cells. NA also aids in the release of replicated virus from the infected cell. In response to EIV infection, the infected equine host cell generates antibodies against HA that can prevent attachment of the virus to the cell. [See in general, Myers and Wilson, *Clinical Techniques in Equine Practice*, 5 (3):187-196 (2006)].

Due to the risk of sudden and widespread outbreaks of respiratory disease caused by the highly contagious EIV, vaccines containing HA antigens (e.g., killed EIV isolates) have been developed and successfully employed in equine. Of the sixteen HA and nine NA subtypes of influenza viruses, the H7N7 (A/equine/1) and the H3N8 (A/equine/2) are the only combinations that have been identified in horses. Moreover, H3N8 is by far the predominant combination found in diseased horses [Myers and Wilson, *Clinical Techniques in Equine Practice*, 5 (3):187-196 (2006)]. However, because influenza virus is an RNA virus, the HA protein is particularly susceptible to genetic and antigenic drift, which consequently leads to vaccine failure. Therefore, there is a great need to identify new EIV isolates that when administered in vaccines to equine provide protection against currently emerging EIV strains, e.g., in the U.S. especially, for use in new safe and efficacious EIV vaccines.

The citation of any reference herein should not be construed as an admission that such reference is available as "prior art" to the instant application.

SUMMARY OF THE INVENTION

Accordingly, the present invention provides new equine influenza virus (EIV) isolates (including isolated EIV isolates) that when administered to equine in vaccines provide protection against currently emerging EIV strains, e.g., in the U.S. especially, which have undergone an antigenic shift. In certain embodiments the new EIV isolates are inactivated (e.g., killed in an unnatural way). The present invention further provides safe and efficacious vaccines that comprise the new EIV isolates, corresponding killed EIV isolates, recombinant expression vectors that encode an EIV hemagglutinin protein (HA) protein or fragment thereof derived from the new EIV isolates, or combinations thereof. The present invention also provides methods of administering such safe and efficacious vaccines to equine.

In particular embodiments, the EIV isolate of the present invention comprises a genome that encodes a HA comprising the amino acid sequence of SEQ ID NO: 4. In more particular embodiments, the EIV isolate comprises a genome that comprises the nucleotide sequence of SEQ ID NO: 3. In related embodiments, the EIV isolate of the present invention comprises a genome that encodes a HA comprising the amino acid sequence of SEQ ID NO: 2. In more particular embodiments, the EIV isolate comprises a genome that comprises the nucleotide sequence of SEQ ID NO: 1.

In certain embodiments, the EIV isolate of the present invention comprises a genome that encodes a HA comprising an amino acid sequence that comprises 90% or greater, 95% or greater, 98% or greater, or 99% or greater identity with the amino acid sequence of SEQ ID NO: 2 and comprises an amino acid residue at position 222 other than that of a tryptophan or an arginine. In other embodiments, the EIV isolate of the present invention comprises a genome that encodes a HA comprising an amino acid sequence that comprises 90% or greater, 95% or greater, 98% or greater, 99% or greater identity with the amino acid sequence of SEQ ID NO: 2 and comprises an amino acid residue at position 222 other than that of a tryptophan or an arginine and either an amino acid residue at position 223 other than that of a valine or an amino acid residue at position 188 other than that of an asparagine. In still other embodiments, the EIV isolate of the present invention comprises a genome that encodes a HA comprising an amino acid sequence that comprises 90% or greater, 95% or greater, 98% or greater, 99% or greater identity with the amino acid sequence of SEQ ID NO: 2 and comprises an amino acid residue at position 222 other than that of a tryptophan or an arginine and an amino acid residue at position 223 other than that of a valine. In yet other embodiments, the EIV isolate of the present invention comprises a genome that encodes a HA comprising an amino acid sequence that comprises 90% or greater, 95% or greater, 98% or greater, 99% or greater identity with the amino acid sequence of SEQ ID NO: 2 and comprises an amino acid residue at position 222 other than that of a tryptophan or an arginine and an amino acid residue at position 188 other than that of an asparagine. In still other embodiments, the EIV isolate of the present invention comprises a genome that encodes a HA comprising an amino acid sequence that comprises 90% or greater, 95% or greater, 98% or greater, 99% or greater identity with the amino acid sequence of SEQ ID NO: 2 and comprises an amino acid residue at position 222 other than that of a tryptophan or an arginine, an amino acid residue at position 223 other than that of a valine, and an amino acid residue at position 188 other than that of an asparagine.

The present invention also provides any of the aforementioned EIV isolates that comprise a genome that encodes a HA that further comprises one or more or all of the following: an amino acid residue other than that of an arginine at position 62, an amino acid residue other than that of an aspartic acid at position 104, an amino acid residue other than that of an alanine at position 138, and an amino acid residue other than that of a glycine at position 7.

In more particular embodiments, the EIV isolate of the present invention comprises a genome that encodes a HA comprising an amino acid sequence that comprises 90% or greater, 95% or greater, 98% or greater, 99% or greater identity with the amino acid sequence of SEQ ID NO: 2 and comprises a leucine residue at position 222. In other embodiments, the EIV isolate of the present invention comprises a genome that encodes a HA comprising an amino acid sequence that comprises 90% or greater, 95% or greater, 98% or greater, 99% or greater identity with the amino acid sequence of SEQ ID NO: 2 and comprises both an isoleucine residue at position 223 and a threonine residue at position 188.

In still other embodiments, the EIV isolate of the present invention comprises a genome that encodes a HA comprising an amino acid sequence that comprises 90% or greater, 95% or greater, 98% or greater, 99% or greater identity with the amino acid sequence of SEQ ID NO: 2 and comprises a leucine residue at position 222 and an isoleucine at position 223. In yet other embodiments, the EIV isolate of the present invention comprises a genome that encodes a HA comprising an amino acid sequence that comprises 90% or greater, 95% or greater, 98% or greater, 99% or greater identity with the amino acid sequence of SEQ ID NO: 2 and comprises a leucine residue at position 222 and a threonine residue at position 188.

In yet other embodiments, the EIV isolate of the present invention comprises a genome that encodes a HA comprising an amino acid sequence that comprises 90% or greater, 95% or greater, 98% or greater, 99% or greater identity with the amino acid sequence of SEQ ID NO: 2 and comprises a leucine residue at position 222, an isoleucine residue at position 223, and a threonine residue at position 188.

The present invention further provides any of the aforementioned EIV isolates that comprise a genome that encodes a HA that further comprises one or more or all of the following: a lysine residue at position 62, an asparagine residue at position 104, a serine residue at position 138, and an aspartic acid residue at position 7.

In specific embodiments the EIV isolate (e.g., an isolated EIV isolate) comprises the identifying characteristics of ATCC accession No. PTA-121715, (Equine Influenza Virus A/Eq/Florida/2013). In more specific embodiments of this type, the EIV isolate (e.g., an isolated EIV isolate) is ATCC accession No. PTA-121715. Progeny and/or derivatives of the ATCC accession No. PTA-121715 isolate are also part of the present invention.

All of the EIV isolates of the present invention can be inactivated (i.e., killed). In particular embodiments the EIV isolates are killed in an unnatural manner. In certain embodiments of this type, the EIV isolate is killed with a synthetic agent. In other embodiments, the EIV isolate is killed with an acidic solution (e.g., pH 1-3 for 30-60 minutes). In yet other embodiments, the EIV isolate is killed by heating the isolate at a temperature higher than equine body temperature, but below boiling (e.g., 45°-90°, or 60°-80° C.) for 30 minutes or more. In a particular embodiment of this type the EIV isolate is killed by heating it at 60°-80° C. for 30 to 60 minutes. In still another embodiment of this type the EIV isolate is killed by treating at 60°-80° C. for 30 to 120 minutes. In yet another embodiment of this type the EIV isolate is killed by treating at 60°-80° C. for 30 to 180 minutes.

The present invention further provides recombinant, isolated, or isolated recombinant hemagglutinin proteins (HA) proteins. In particular embodiments, the HA comprises the amino acid sequence of SEQ ID NO: 4. In related embodiments, the HA comprises the amino acid sequence of SEQ ID NO: 2.

In certain embodiments, the HA comprises an amino acid sequence that comprises 90% or greater, 95% or greater, 98% or greater, 99% or greater identity with the amino acid sequence of SEQ ID NO: 2 and comprises an amino acid residue at position 222 other than that of a tryptophan or an arginine. In other embodiments, the HA comprises an amino acid sequence that comprises 90% or greater, 95% or greater, 98% or greater, 99% or greater identity with the amino acid sequence of SEQ ID NO: 2 and comprises both an amino acid residue at position 223 other than that of a valine and an amino acid residue at position 188 other than that of an asparagine. In still other embodiments, the HA comprises an amino acid sequence that comprises 90% or greater, 95% or greater, 98% or greater, 99% or greater identity with the amino acid sequence of SEQ ID NO: 2 and comprises an amino acid residue at position 222 other than that of a tryptophan or an arginine, and an amino acid residue at position 223 other than that of a valine. In yet other embodiments, the HA comprises an amino acid sequence that comprises 90% or greater, 95% or greater, 98% or greater, 99% or greater identity with the amino acid sequence of SEQ ID NO: 2 and comprises an amino acid residue at position 222 other than that of a tryptophan or an arginine, and an amino acid residue at position 188 other than that of an asparagine. In still other embodiments, the HA comprises an amino acid sequence that comprises 90% or greater, 95% or greater, 98% or greater, 99% or greater identity with the amino acid sequence of SEQ ID NO: 2 and comprises an amino acid residue at position 222 other than that of a tryptophan or an arginine, an amino acid residue at position 223 other than that of a valine, and an amino acid residue at position 188 other than that of an asparagine.

The present invention also provides any of the aforementioned HAs that further comprise one or more or all of the following: an amino acid residue other than that of an arginine at position 62, an amino acid residue other than that of an aspartic acid at position 104, an amino acid residue other than that of an alanine at position 138, and an amino acid residue other than that of a glycine at position 7.

In more particular embodiments, the HA comprises an amino acid sequence that comprises 90% or greater, 95% or greater, 98% or greater, 99% or greater identity with the amino acid sequence of SEQ ID NO: 2 and comprises a leucine residue at position 222. In other embodiments, the HA comprises an amino acid sequence that comprises 90% or greater, 95% or greater, 98% or greater, 99% or greater identity with the amino acid sequence of SEQ ID NO: 2 and comprises both an isoleucine residue at position 223 and a threonine residue at position 188. In still other embodiments, the HA comprises an amino acid sequence that comprises 90% or greater, 95% or greater, 98% or greater, 99% or greater identity with the amino acid sequence of SEQ ID NO: 2 and comprises a leucine residue at position 222 and an isoleucine at position 223.

In yet other embodiments, the HA comprises an amino acid sequence that comprises 90% or greater, 95% or greater, 98% or greater, 99% or greater identity with the amino acid sequence of SEQ ID NO: 2 and comprises a leucine residue at position 222 and a threonine residue at position 188. In still other embodiments, the HA comprises an amino acid sequence that comprises 90% or greater, 95% or greater, 98% or greater, 99% or greater identity with the amino acid sequence of SEQ ID NO: 2 and comprises a leucine residue at position 222, an isoleucine residue at position 223, and a threonine residue at position 188. The present invention further provides any of the aforementioned HAs that further comprises one or more or all of the following: a lysine residue at position 62, an asparagine residue at position 104, a serine residue at position 138, and an aspartic acid residue at position 7.

The present invention also provides antigenic fragments of the HAs of the present invention as well as nucleic acids that encode the HAs and antigenic fragments thereof. In particular embodiments the nucleic acid comprises the nucleotide sequence of SEQ ID NO: 3. In related embodiments the nucleic acid comprises the nucleotide sequence of SEQ ID NO: 1.

In addition, the present invention provides recombinant expression vectors that encode the HAs and antigenic fragments thereof of the present invention. In such constructs, the nucleic acids that encode the HAs and antigenic fragments thereof of the present invention can be operatively linked to an expression control sequence. In certain embodiments the recombinant expression vector is a recombinant virus vector. In more particular embodiments, the recombinant expression vector is a canine parainfluenza virus.

The present invention further provides immunogenic compositions (including multivalent immunogenic compositions) and vaccines (including multivalent vaccines) that comprise one or more of the EIVs of the present invention and a pharmaceutically acceptable carrier. In particular embodiments the EIVs are inactivated EIVs of the present invention. In more particular embodiments the inactivated EIVs are EIVs killed in an unnatural way. The immunogenic compositions and vaccines can further comprise a clade 2 EIV. In particular embodiments the clade 2 EIV is an Equine Influenza Virus/Eq/Richmond/1/2007. In other embodiments the clade 2 EIV is an A/Shropshire/1/10. In still other embodiments the clade 2 EIV is an East Renfrewshire/2/11. In yet other embodiments the clade 2 EIV is a Northamptonshire/1/13. In still other embodiments combinations of two or more of these clade 2 EIVs are included in the multivalent vaccine. In particular embodiments the clade 2 EIVs are inactivated clade 2 EIVs. In more particular embodiments the clade 2 EIVs are inactivated. In even more particular embodiments the inactivated clade 2EIVs are clade 2EIVs killed in an unnatural way.

The multivalent vaccines can further comprise antigens from one or more of the following: Equine Herpesvirus, Equine Rhinitis virus, Equine Arteritis virus, Equine Rotavirus, *Neorickettsia risticii* (*N. risticii*), Equine Rotavirus, Hendra virus, Eastern Encephalomyelitis, Western Encephalomyelitis, Venezuelan Encephalomyelitis, Japanese Encephalomyelitis, Equine Infectious Anemia virus, *Corynebacterium pseudotuberculosis*, *Clostridium* tetanus (Tetanus), rabies virus (Rabies), West Nile virus, *Rhodococcus equi*, *Streptococcus equi*, and Flavirus chimera.

In related embodiments the pharmaceutically acceptable carrier is not a product of nature. In one such embodiment, a pharmaceutically acceptable preservative is selected from the group consisting of gentamicin sulfate and thimerosal. In certain embodiments the immunogenic compositions or vaccines comprise an adjuvant. In particular embodiments of this type the adjuvant comprises a synthetic component. In one such embodiment, the adjuvant is an immunostimulatory complex.

The present invention further provides methods of immunizing an equine against EIV comprising administering an immunogenic composition (including multivalent immunogenic compositions) of the present invention and/or a vaccine (including multivalent vaccines) of the present invention to an equine.

These and other aspects of the present invention will be better appreciated by reference to the following Figures and the Detailed Description.

BRIEF DESCRIPTION OF THE DRAWINGS

FIG. 1 depicts the alignment of the HA protein sequences of the A.Eq.Ohio.2003 (OH03) and A.Eq.Florida.2013 (FL13) EIV isolates. The amino acid residues in the HA of EIV FL13 that differ from that of the HA of OH03 are boxed. Both sequences include the 15 amino acid residue signal peptide. The position of the amino acid residue changes in the boxes is numbered based on their position in mature protein, i.e., without the signal peptide. The entire amino acid sequence of the HA proteins are provided, with 1Q to 329R being the HA1 region and 330G to 504G being the HA2 region.

FIG. 2 depicts the alignment of mature HA amino acid sequences of the human influenza HK68, EIV OH03, and FL13 isolates. The sequences for the mature HA proteins (i.e., without the signal peptides) are listed. The HA sequences include both the HA1 and the HA2 region. The amino acid residues in EIV FL13 and EIV OH03 that differ from A.human.HK.1968 are boxed.

Figure 3:
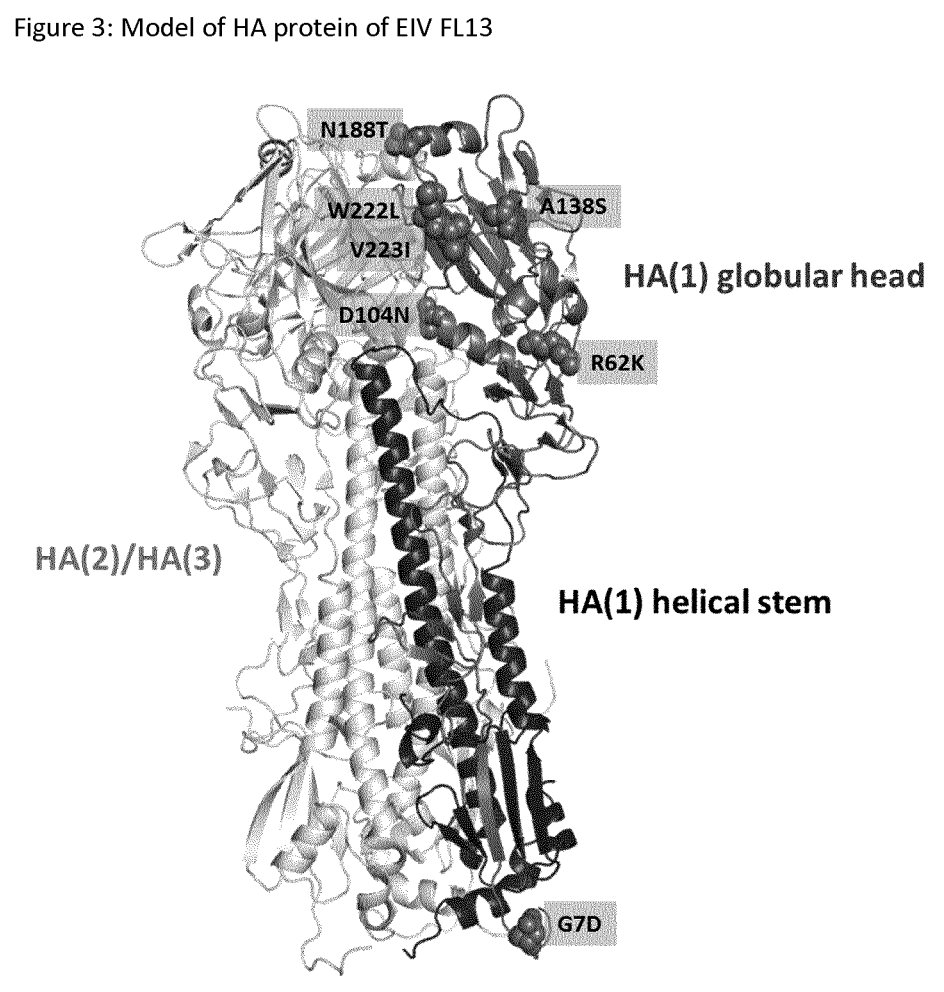

FIG. 3 depicts the structure modeling of the HA protein of EIV FL13 on the human Flu H3N2 HA structure as a schematic representation of the structural model of the HA protein of EIV FL13 as a homotrimer. The model was built using human influenza virus H3N2 (pdb 2HMG) as the template. One HA monomer [HA(1)] is shown in darker shades. Differences (e.g., mutations) between the HA of the FL13 compared with that of the OH03 (G7D, R62K, D104N, A138S, N188T, W222L, V223I) are mapped onto HA1 and the residues are labeled and shown as space-fill models.

FIG. 4 shows the location of mutations and the HA neutralizing antibody epitopes mapped on the modelled FL13 HA structure. The epitopes of neutralizing antibodies (nAbs) HC45 and HC63, as well as the receptor binding site (RBS) are mapped onto the structure model of FL13 HA (represented by space-fill models of different shades). The mutated residues are also labeled and highlighted (dark spheres). R62K is located at the middle of the HC45 epitope, whereas N188T and A138S are at the periphery of the HC63 epitope and RBS, respectively. W222L and V223I are in the vicinity of RBS. D104N is further away from RBS and is buried.

FIGS. 5a-5b show the location of R62K in the HC45 epitope and its potential effects on antibody binding. FIG. 5a depicts the amino acid residues of the HC45 epitope on the HA surface. R62K is at the center of the HC45 epitope. FIG. 5b depicts the interactions of R62K with Tyr32 of the neutralizing antibody (nAb) HC45. Both arginine and lysine are capable of making cation-pi interactions with Tyr 32 of HC45. However, the lysine residue is not able to make the pi-pi interactions that the arginine residue can.

FIGS. 6a-6b show the location of N188T in the HC63 epitope and its potential effect on antibody binding. FIG. 6a shows the residues in the HC63 epitope and the location of N188T (at the periphery of HC63 epitope). FIG. 6b depicts the impact of N188T change (mutation) on the HA association with HC63: N188 from HA(1) is involved in polar interactions with 8201 and N246 of HA(2). For reference, the side chain of T188 is also indicated (white stick).

FIGS. 7a-7b show the location of A138S, W222L and V223I and the receptor binding site (RBS). FIG. 7a shows the amino acid residues (sticks) in the RBS region mapped onto the HA protein (surface). A138S is at the perimeter of the RBS. FIG. 7b shows the close-up view of spatial arrangement of residues A138S, W222L, V223I, and the RBS key residue Y98, as space-fill models.

DETAILED DESCRIPTION OF THE INVENTION

Accordingly, the present invention provides equine influenza virus (EIV) isolates (including isolated EIV isolates) that comprise a genome that encodes a hemagglutinin protein (HA) comprising an amino acid sequence that previously had not been identified. Moreover, the present invention provides EIV isolates that have unique combinations of amino acid residue changes within regions of the HA protein that had been recognized by antibodies raised against earlier isolates. The present invention further employs three-dimensional structural modeling to correlate alterations in the amino acid sequence of the HA proteins of the EIV isolates of the present invention with the ability of antibodies raised against earlier isolates to recognize those earlier isolates. The present invention also provides immunogenic compositions (including multivalent immunogenic compositions) and vaccines (particularly safe and efficacious vaccines and multivalent) that can be used to aid in the protection of respiratory disease in horses.

The use of singular terms for convenience in the description is in no way intended to be so limiting. Thus, for example, reference to a "virus" includes reference to one or more of such viruses, unless otherwise specified. The use of plural terms is also not intended to be limiting, unless otherwise specified.

As used herein, the term, "approximately," is used interchangeably with the term "about" and generally signifies that a value is within twenty-five percent of the indicated value, unless otherwise indicated, e.g., a time of "about" 60 minutes can be 45 minutes to 75 minutes.

As used herein, a "vaccine" is a composition that is suitable for application to an animal (e.g., horses) which upon administration to the animal induces an immune response strong enough to minimally aid in the protection from a clinical disease arising from an infection with a wild-type micro-organism, i.e., strong enough for aiding in the prevention of the clinical disease, and/or preventing, ameliorating, or curing the clinical disease. Unless expressly indicated otherwise, the use of the term vaccine includes multivalent vaccines.

As used herein, a "multivalent vaccine" is a vaccine that comprises two or more different antigens. In a particular embodiment of this type, the multivalent vaccine stimulates the immune system of the recipient against two or more different pathogens.

As used herein, a "liquid stable" vaccine is a vaccine maintained as a liquid (including a liquid multivalent vaccine) that remains efficacious for at least one year when stored at or below 7° C. (e.g., in a standard refrigerator, and/or at 0° C.-7° C.). In particular embodiments a liquid stable vaccine remains efficacious when stored at or below 7° C. for at least 1.5 years. In more particular embodiments a liquid stable vaccine remains efficacious when stored at or below 7° C. for at least 2 years. In still more particular embodiments a liquid stable vaccine remains efficacious when stored at or below 7° C. for at least 2.5 to 3 years. Examples of liquid stable vaccines are provided in U.S. application Ser. No. 14/202,454 filed on Mar. 10, 2014, and U.S. application Ser. No. 14/202,194 filed on Mar. 10, 2014, the contents of both of which are hereby incorporated by reference in their entireties.

As used herein, the terms "protect", "protecting", "provide protection to", "providing protection to", and "aids in the protection" do not require complete protection from any indication of infection. For example, "aids in the protection" can mean that the protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection.

The term "prophylactically-effective amount" refers to the amount of a composition that when administered to equine significantly reduces the likelihood and/or extent of an infection/infestation due to a given pathogen.

"Metaphylaxis" is the timely mass medication of an entire group of animals to eliminate or minimize an expected outbreak of disease, e.g. in one or more animals at high risk of infection/infestation. In one particular embodiment, high risk foals are light weight, young horses with unknown health histories.

The term "chemoprophylaxis" refers to the administration of a medication/treatment, e.g., one or more prophylactic compositions, for the purpose of preventing or reducing viral, bacterial, and/or parasitic infection/infestation; and/or preventing or reducing disease and/or symptoms related to that infection/infestation.

The term "prophylactic composition" refers to any agent used singularly or in combination with other agents that significantly reduces the likelihood and/or extent of an infection/infestation due to a given pathogen in equine. In one such embodiment the equine are at risk of developing equine respiratory disease.

As used herein the term "inactivated" as it modifies the term "virus", e.g., an inactivated EIV isolate, is used interchangeably with the term "killed", e.g., a killed EIV isolate, and is a virus that has lost its ability to replicate due e.g., to an act of man, but still retains the ability of having the immune system recognize it. ("Inactivated" is often used rather than "killed" to refer to viral vaccines, as viruses are generally not considered to be alive.)

As used herein the term "killed in an unnatural way" as it modifies the term "virus" indicates that the virus has been inactivated in a manner that does not naturally occur in nature. For example, a virus that has been inactivated by heating the virus above 60° C. (e.g., 60-80° C.) for about 30 minutes or more has been killed in an unnatural way because viruses are not naturally found at such high temperatures.

As used herein, the term "therapeutically effective amount" is an amount of a given antigen, e.g., a killed equine influenza virus, which is sufficient to provide protection to and/or aid in the protection from the pathogen that the antigen is being administered to protect against, when provided in a single administration and/or when intended, provided as an initial administration with one or more subsequent booster administration(s).

As used herein, an "efficacious" vaccine comprises a therapeutically effective amount of a given antigen. An "efficacious" vaccine retains sufficient titer for a given antigen to be compliant with the regulatory requirements for that antigen for the jurisdiction where the vaccine is administered, e.g., the administration of a vaccine in the United States is governed by the United States Department of Agriculture (USDA).

As used herein, an "immune response" refers to the subject animal's active immunity due to having received one or more vaccines. The immune response can include the production of antibodies to the antigen or immunogen present in the vaccine. "Immune response" in a subject refers to the development of a humoral immune response, a cellular immune response, or a humoral and a cellular immune response to an antigen. Immune responses may be measured using standard immunoassays and neutralization assays, which are known in the art.

As used herein, the term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient.

The term "carrier" refers to a diluent, adjuvant, excipient, or vehicle with which the compound is administered. Pharmaceutical acceptable carriers can be sterile liquids, such as water and/or oils, including those of petroleum, animal, vegetable or synthetic origin, such as peanut oil, soybean oil, mineral oil, sesame oil, cellulose acetate, and the like. Water or aqueous solution saline solutions and aqueous sugar, e.g., dextrose and/or glycerol solutions can be employed as carriers, particularly for injectable solutions. Other pharmaceutical acceptable carriers include iminocarbonates, proteinoid microspheres, polyanhydrides, and the like. In addition, the carrier can be and/or comprise a hydrocolloid and/or polymer solution e.g., to thicken the equine vaccines that are to be sprayed onto the horses, e.g., foals.

As used herein a "pharmaceutically acceptable carrier" that is not a "product of nature" is a pharmaceutically acceptable carrier that is not found in nature. Examples of pharmaceutically acceptable carrier that are not a "product of nature" include man-made polymers.

As used herein, a "substance that that is not naturally found in nature" or a "synthetic component" and the like are substances (e.g., chemical compound) which uniquely exist due to an act of man. Of course, all substances that are not naturally found in nature must be derived or originate from substances that are.

As used herein, an "adjuvant" is a substance that is able to favor or amplify the cascade of immunological events, ultimately leading to a better immunological response, i.e., the integrated bodily response to an antigen. An adjuvant is in general not required for the immunological response to occur, but favors or amplifies this response. In particular embodiments an adjuvant can comprise a one or more synthetic components. Examples of adjuvant components include polylactide-co-glycolides (PLG), and immunstimulatory complexes (ISCOMS).

A nucleotide sequence is "operatively linked" to an expression control sequence when the expression control sequence controls or regulates the transcription and translation of that nucleotide sequence. The term operatively linked includes having an appropriate start signal.

Transcriptional and translational control sequences are nucleic acid (e.g., DNA or RNA) regulatory sequences, such as promoters, enhancers, terminators, and the like, that provide for the expression of a coding sequence in a host cell. In eukaryotic cells, polyadenylation signals are control sequences.

A coding sequence is "under the control" of transcriptional and translational control sequences in a cell when RNA polymerase transcribes the coding sequence into mRNA, which can then be trans-RNA spliced, if, when, and where appropriate, and translated into the protein encoded by the coding sequence.

A "heterologous nucleotide sequence" as used herein is a nucleotide sequence that is added by recombinant methods to a nucleotide sequence encoding a polypeptide of the present invention or encoding a fragment thereof (i.e., an antigenic fragment), to form a nucleic acid that is not naturally formed in nature. Such nucleic acids can e.g., encode chimeric proteins. In addition, as used herein, a heterologous nucleotide sequence need not be a single contiguous nucleotide sequence, but can include multiple non-contiguous nucleotide sequences that have been combined with a nucleotide sequence encoding a polypeptide of the present invention, or a portion thereof. A heterologous nucleotide sequence can comprise non-coding sequences including restriction sites, regulatory sites, promoters and the like. In still another embodiment the heterologous nucleotide can function as a means of detecting a nucleic acid of the present invention.

As used herein one amino acid sequence is 100% "identical" to a second amino acid sequence when the amino acid residues of both sequences are identical. Accordingly, an amino acid sequence is 50% "identical" to a second amino acid sequence when 50% of the amino acid residues of the two amino acid sequences are identical. The sequence comparison is performed over a contiguous block of amino acid residues comprised by a given protein, e.g., a protein, or a portion of the polypeptide being compared. In a particular embodiment, selected deletions or insertions that could otherwise alter the correspondence between the two amino acid sequences are taken into account.

As used herein, nucleotide and amino acid sequence percent identity can be determined using C, MacVector (MacVector, Inc. Cary, N.C. 27519), Vector NTI (Informax, Inc. MD), Oxford Molecular Group PLC (1996) and the Clustal W algorithm with the alignment default parameters, and default parameters for identity. These commercially available programs can also be used to determine sequence similarity using the same or analogous default parameters. Alternatively, an Advanced Blast search under the default filter conditions can be used, e.g., using the GCG (Genetics Computer Group, Program Manual for the GCG Package, Version 7, Madison, Wis.) pileup program using the default parameters.

As used herein the term "antigenic fragment" of a HA protein of the present invention is a fragment of the amino acid sequence of SEQ ID NO: 2 (or corresponding recombinant peptide) that is antigenic, and retains between 25 to 500 contiguous amino acid residues of SEQ ID NO: 2 that includes the leucine residue at position 222 and the isoleucine at position 223 of SEQ ID NO: 2. In certain embodiments, the antigenic fragment contains 50 amino acid contiguous residues or more, but fewer than 350 contiguous amino acid residues of the amino acid sequence of SEQ ID NO: 2, but includes the leucine residue at position 222 and the isoleucine at position 223 of SEQ ID NO: 2. In still another embodiment, the antigenic fragment comprises 75 contiguous amino acid residues or more of SEQ ID NO: 2, but fewer than 250 contiguous amino acid residues, but includes the leucine residue at position 222 and the isoleucine at position 223 of SEQ ID NO: 2. In yet another embodiment, the antigenic fragment contains 150 contiguous amino acid residues or more of SEQ ID NO: 2, but fewer than 200 contiguous amino acid residues of SEQ ID NO: 2, but includes the leucine residue at position 222 and the isoleucine at position 223 of SEQ ID NO: 2. In particular embodiments, the antigenic fragment further comprises at least one, two, three, four, or five additional amino acid residues from the following: the threonine residue at position 188, the serine residue at position 138, the asparagine residue at position 104, the lysine residue at position 62, and/or the aspartic acid residue at position 7 of the amino acid sequence of SEQ ID NO: 2.

An antigenic fragment of an HA protein of the present invention can be obtained from a recombinant source, from a protein isolated from natural sources, or through chemical synthesis. Similarly, an antigenic fragment can be obtained following the proteolytic digestion of such HA proteins or fragments thereof. Alternatively, an antigenic fragment of the present invention can be generated by recombinant expression, or alternatively, through peptide synthesis.

As used herein, "systemic administration" is administration into the circulatory system of the body (comprising the cardiovascular and lymphatic system), thus affecting the body as a whole rather than a specific locus such as the gastro-intestinal tract (via e.g., oral or rectal administration) and the respiratory system (via e.g., intranasal administration). Systemic administration can be performed e.g., by administering into muscle tissue (intramuscular), into the dermis (intradermal, transdermal, or supradermal), underneath the skin (subcutaneous), underneath the mucosa (submucosal), in the veins (intravenous) etc.

"Parenteral administration" includes subcutaneous injections, submucosal injections, intravenous injections, intramuscular injections, intradermal injections, and infusion.

As used herein "intranasal administration" of a vaccine to an animal subject or "intranasally administering" a vaccine to an animal subject refers to applying or administering that vaccine to/through the nose and/or nasal cavity.

Preparation of Killed and/or Attenuated EIV:

Inactivation of an EIV isolate of the present invention can be accomplished by treating the virus with inactivation chemicals [e.g., formalin, formaldehyde, beta propiolactone ("BPL"), bromoethylamine ("BEA"), and binary ethylenimine ("BEI")] or by non-chemical methods [e.g., heat, freeze/thaw, ultraviolet irradiation, acidic conditions, high voltage electrostatic fields, or sonication] to disable or decrease the replication capacity of the virus. In addition, the EIVs can be inactivated by treatment with certain detergents. Heat inactivation can be performed at 60° C. to 80° C. for about 30 to about 60 minutes. In certain cases the heat inactivation can be carried out for about 1 to about 12 hours.

Alternatively, live attenuated vaccines may be prepared by the conventional means. Conventional means generally include, for example, modifying pathogenic strains by in vitro passaging, cold adaptation, modifying the pathogenicity of the organism by genetic manipulation, preparation of chimeras, insertion of antigens into viral vectors, selecting non-virulent wild type strains, and other methods well known to the skilled artisan.

In certain embodiments, the live attenuated EIV strain is derived by serial passage of the wild-type virus through cell culture. In alternative embodiments, an attenuated strain is derived by serial passage of the wild-type virus through laboratory animals, non-host animals, or eggs. The accumulation of genetic mutation during such passage(s) typically leads to progressive loss of virulence of the organism to the original host.

In particular embodiments, the live attenuated virus strain is prepared by co-infection of permissible cells with an attenuated mutant virus and pathogenic virus. The desired resultant recombinant virus has the safety of the attenuated virus with genes coding for protective antigens from the pathogenic virus.

In other embodiments, the live attenuated virus strain is prepared by cold adaptation. A cold-adapted virus has an advantage of replicating only at the temperature found in upper respiratory tract. A method of generation of a cold-adapted equine influenza virus has been described in U.S. Pat. No. 6,177,082 [hereby incorporated by reference in its entirety]. A desired resulting cold-adapted virus confers one or more of the following phenotypes: cold adaptation, temperature sensitivity, dominant interference, and/or attenuation.

In specific embodiments, the live attenuated virus strain is prepared by recombinant means, such as by homologous recombination, a point mutation, deletion, or insertion to convert a pathogenic virus to a non-pathogenic or less-pathogenic virus compared to the original virus, while preserving the protective properties of the original virus.

Nucleic Acids Encoding the Hemagglutinin Proteins of the Present Invention

A nucleic acid, such as a cDNA, that encodes a HA of the present invention, can be placed into a vector, e.g., a recombinant bacterial host cell, to express a protein and/or antigen of the present invention. Alternatively, the vector can be a recombinant virus (e.g., a canarypox virus) to be used in immunogenic compositions such as vaccines.

In addition, obtaining and/or constructing a DNA that encodes a HA of the present invention, including antigenic fragments thereof, facilitates the production of economically important quantities of the protein or antigenic fragments thereof. The large quantities of the proteins and/or antigenic fragments thereof produced are useful for making certain vaccines of the present invention.

Accordingly, the present invention also provides nucleotide constructs that allow for the expression and isolation of large quantities of the proteins and/or antigens of the present invention, such as the HA. These nucleic acids can further contain heterologous nucleotide sequences. To express a recombinant protein of the present invention in a host cell, an expression vector can be constructed comprising the corresponding cDNA. The present invention therefore, provides expression vectors containing nucleic acids encoding the HAs of the present invention, including variants thereof, and/or antigenic fragments thereof and/or chimeric proteins.

Due to the degeneracy of nucleotide coding sequences, other DNA sequences which encode substantially the same amino acid sequence as a nucleic acid encoding a HA of the present invention may be used in the practice of the present invention. These include, but are not limited to, allelic genes, homologous genes from other strains, and/or those that are altered by the substitution of different codons that encode the same amino acid residue within the sequence, thus producing a silent change. Host cells comprising the expression vectors of the present invention are also provided. One particular host cell is an *E. coli* cell.

General methods for the cloning of cDNAs and expression of their corresponding recombinant proteins have been described [see Sambrook and Russell, *Molecular Cloning, A laboratory Manual*, 3<sup>rd</sup> edition, Cold Spring Harbor Laboratory Press, Cold Spring Harbor L.I. (2000)]. Preferably, all of the nucleic acid constructs of the present invention are sequence confirmed.

In addition, any technique for mutagenesis known in the art can be used to modify a HA of the present invention, including but not limited to, in vitro site-directed mutagenesis [Hutchinson et al., *J. Biol. Chem.*, 253:6551 (1978); Zoller and Smith, *DNA*, 3:479-488 (1984); Oliphant et al., *Gene*, 44:177 (1986); Hutchinson et al., *Proc. Natl. Acad. Sci. U.S.A.*, 83:710 (1986); Wang and Malcolm, *BioTechniques* 26:680-682 (1999) the contents of which are hereby incorporated by reference in their entireties]. The use of TAB@ linkers (Pharmacia), etc. and PCR techniques also can be employed for site directed mutagenesis [see Higuchi, "Using PCR to Engineer DNA", in PCR Technology: Principles and Applications for DNA Amplification, H. Erlich, ed., Stockton Press, Chapter 6, pp. 61-70 (1989)].

Recombinant Vectors

The present invention also provides vectors that comprise the nucleic acids and express the proteins of the present invention. Such vectors can contain one or more nucleotide sequences and/or heterologous sequences of the present invention operatively linked to an expression control sequence. In certain embodiments the vector is an animal virus vector. Examples of such vectors include adenoviruses, vaccinia virus, herpesviruses, poxviruses e.g., canarypox virus, paramyxoviruses, rhabdoviruses, and baculoviruses. In other embodiments, the vector is a plasmid or a bacterium such as *E. coli* or *Bordetella bronchiseptica* [see, U.S. Pat. No. 8,821,852, the contents of which are hereby incorporated by reference in their entireties]. In another embodiment the recombinant virus is a parainfluenza virus. Any of the recombinant vectors of the present invention can be used in an immunogenic composition and/or a vaccine.

Hemagglutinin of the Present Invention

The present invention provides isolated and/or recombinant HAs, including antigen fragments and chimeric proteins thereof. In addition, HAs containing altered sequences in which functionally equivalent amino acid residues are substituted for those within the amino acid sequence resulting in a conservative amino acid substitution are also provided by the present invention.

Thus, one or more of these amino acid residues within the sequence can possibly be substituted by another amino acid of a similar polarity, which can, but not necessarily, act as a functional equivalent, resulting in a silent alteration. Substitutes for an amino acid within the sequence may be selected from other members of the class to which the amino acid belongs. For example, the nonpolar amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine and lysine. The negatively charged (acidic) amino acids include aspartic acid and glutamic acid.

Particularly preferred conserved amino acid exchanges are:

(a) Lys for Arg or vice versa such that a positive charge may be maintained;

(b) Glu for Asp or vice versa such that a negative charge may be maintained;

(c) Ser for Thr or vice versa such that a free —OH can be maintained;

(d) Gln for Asn or vice versa such that a free $NH_2$ can be maintained; and (e) Ile for Leu or for Val or vice versa as being roughly equivalent hydrophobic amino acids.

All of the HAs of the present invention, including antigenic fragments thereof, also can be part of a chimeric protein. In a specific embodiment, a chimeric polypeptide is expressed in a prokaryotic cell. Such a chimeric protein can be a fusion protein used to isolate a HA of the present invention, through the use of an affinity column that is specific for a protein fused to the HA, for example. Examples of such fusion proteins include: a glutathione-S-transferase (GST) fusion protein, a maltose-binding protein (MBP) fusion protein, a FLAG-tagged fusion protein, or a poly-histidine-tagged fusion protein. Specific linker sequences such as a Ser-Gly linker can also be part of such a fusion protein.

Indeed, the expression of one or more of the inventive proteins, as a fusion protein, can facilitate stable expression, and/or allow for purification based on the properties of the fusion partner. Thus the purification of the recombinant HAs of the present invention can be simplified through the use of fusion proteins having affinity Tags. For example, GST binds glutathione conjugated to a solid support matrix, MBP binds to a maltose matrix, and poly-histidine chelates to a Ni-chelation support matrix [see Hochuli et al., *Biotechnology* 6:1321-1325 (1998)].

The fusion protein can be eluted from the specific matrix with appropriate buffers, or by treating with a protease that is specific for a cleavage site that has been genetically engineered in between the HA, for example, and its fusion partner. Alternatively, a HA can be combined with a marker protein such as green fluorescent protein [Waldo et al., *Nature Biotech.* 17:691-695 (1999); U.S. Pat. No. 5,625,048 and WO 97/26333, the contents of which are hereby incorporated by reference in their entireties].

Alternatively or in addition, other column chromatography steps (e.g., gel filtration, ion exchange, affinity chromatography etc.) can be used to purify the recombinant polypeptides of the present invention (see below). In many cases, such column chromatography steps employ high performance liquid chromatography or analogous methods in place of the more classical gravity-based procedures.

In addition, a HA of the present invention or an antigenic fragment thereof can be chemically synthesized [see e.g., Synthetic Peptides: *A User's Guide*, W.H. Freeman & Co., New York, N.Y., pp. 382, Grant, ed. (1992)].

Antibodies to the Hemagglutinin Proteins of the Present Invention

The HAs of the present invention, and antigenic fragments thereof, as produced by a recombinant source, or through chemical synthesis, or as isolated from natural sources; and variants, derivatives or analogs thereof, including fusion proteins, may be used as an immunogen to generate antibodies. Such antibodies include but are not limited to polyclonal, monoclonal, chimeric including single chain, Fab fragments, and a Fab expression library. Such antibodies can be used in diagnostic kits or as components in vaccines.

Specific anti-HA antibodies of the invention, for example, may be cross-reactive, that is, they may recognize closely-related HAs obtained from a different source (e.g., a different EIV isolate). Polyclonal antibodies have greater likelihood of cross-reactivity. Alternatively, an antibody of the invention may be specific for a single form of an inventive protein, for example, such as a specific fragment of the HA protein comprising the amino acid sequence of SEQ ID NO: 2, or a closely related variant thereof.

In a particular aspect of the present invention compositions and uses of antibodies that are immunoreactive with only a HA of the present invention are provided. Such antibodies "bind specifically" to the particular HA respectively, meaning that they bind via antigen-binding sites of the antibody as compared to non-specific binding interactions.

The terms "antibody" and "antibodies" are used herein in their broadest sense, and include, without limitation, intact monoclonal and polyclonal antibodies as well as fragments such as Fv, Fab, and F(ab') fragments, single-chain antibodies such as scFv, and various chain combinations. The antibodies may be prepared using a variety of well-known methods including, without limitation, immunization of animals having native or transgenic immune repertoires, phage display, hybridoma and recombinant cell culture.

Both polyclonal and monoclonal antibodies may be prepared by conventional techniques. [See, for example, *Monoclonal Antibodies, Hybridomas: A New Dimension in Biological Analyses*, Kennet et al. (eds.), Plenum Press, New York 37 (1980); and *Antibodies: A Laboratory Manual*, Harlow and Land (eds.), Cold Spring Harbor Laboratory Press, Cold Spring Harbor, N.Y., (1988)].

Various procedures known in the art may be used for the production of polyclonal antibodies to a particular HA, variants or derivatives or analogs thereof. For the production of an antibody, various host animals can be immunized by injection with the HA, variant or a derivative (e.g., or fusion protein) thereof or fragment thereof, including but not limited to rabbits, mice, rats, sheep, goats, etc. In one embodiment, the inventive protein can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, aluminum phosphate, surface active substances such as lysolecithin, pluronic polyols, polyanions, peptides, oil emulsions, keyhole limpet hemocyanins, and dinitrophenol.

For preparation of monoclonal antibodies directed toward a given inventive protein, variant, or analog, or derivative thereof, any technique that provides for the production of antibody molecules by continuous cell lines in culture may be used. These include but are not limited to the hybridoma technique originally developed by Kohler and Milstein [*Nature,* 256:495-497 (1975)], as well as the trioma technique, and the human B cell hybridoma technique [Kozbor et al., *Immunology Today,* 4:72 (1983); Cote et al., *Proc. Natl. Acad Sci. U.S.A.,* 80:2026-2030 (1983)].

The monoclonal antibodies of the present invention include chimeric antibodies, versions of antibodies originally produced in mice or other non-human animals. Techniques developed for the production of "chimeric antibodies" by splicing the genes from a mouse antibody molecule specific for a given inventive protein, for example, together with genes from a equine antibody of appropriate biological activity can be used. Such chimeric antibodies are within the scope of this invention [see in general, Morrison et al., *J Bacteriol,* 159:870 (1984); Neuberger et al., *Nature,* 312: 604-608 (1984); Takeda et al., *Nature,* 314:452-454 (1985)].

Vaccines and Multivalent Vaccines

The vaccines of the present invention can comprise any of the EIV isolates of the present invention (live attenuated and/or killed), and/or corresponding isolated and/or recombinant HA proteins, and/or novel antigenic fragments of the HA proteins, and/or recombinant nucleic acids encoding the HA proteins and/or encoding antigenic fragments of the HA proteins (including recombinant vectors, such as recombinant viruses, that comprise and express such nucleic acids), either individually or in any combination.

In addition, any of such EIV antigens can be included in a multivalent vaccine. Such multivalent vaccines can comprise live attenuated or killed antigens of and/or from other equine pathogens including subunit antigens and/or corresponding recombinant vectors that expressing such subunit antigens from other equine pathogens. For example, a multivalent vaccine could include a HA antigen of the present invention along with a recombinant myxoma virus expressing a West Nile virus antigen.

The present invention provides monovalent and multivalent equine vaccines. Non-limiting examples of antigens from other pathogens include one or more (including all) of the following: *Clostridium* tetanus (Tetanus), rabies virus (Rabies), *Neorickettsia risticii* (*N. risticii*), Equine Rotavirus, Equine Rhinitis virus, Equine Arteritis virus, Equine Infectious Anemia virus, Hendra virus, Eastern Encephalomyelitis, Western Encephalomyelitis, *Corynebacterium pseudotuberculosis*, Equine Herpesvirus, West Nile virus (including a live attenuated or killed yellow fever/west nile virus chimeric flavivirus, see e.g., US2009/0246233, hereby incorporated by reference in its entirety), Japanese Encephalomyelitis, Venezuelan Encephalomyelitis, *Rhodococcus equi*, and *Streptococcus equi*. Alternatively, a vaccine based upon material according to the present invention may be administered simultaneously with other inactivated (e.g., killed) or live attenuated vaccines.

Vaccine Administration:

The equine influenza virus vaccines of the present invention may be administered by any conventional means, for example, by systemic administration, including by parenteral administration such as, without limitation, subcutaneous or intramuscular administration. The equine influenza virus vaccines of the present invention also may be administered by mucosal administration, such as by intranasal, oral, intratracheal, rectal, and/or ocular administration. Alternatively, the vaccines may be administered via a skin patch, in a delayed release implant, scarification, or topical administration. It is contemplated that an equine virus vaccine of the present invention also may be administered via the drinking water and/or food of the recipient equine. In a particular embodiment, an equine influenza virus vaccine of the present invention comprises a killed EIV.

The vaccines (including multivalent vaccines) of the present invention also may be administered as part of a combination therapy, i.e., a therapy that includes, in addition to the vaccine itself, administering one or more additional active agents, therapies, etc. In that instance, it should be recognized the amount of vaccine that constitutes a "therapeutically effective" amount may be more or less than the amount of vaccine that would constitute a "therapeutically effective" amount if the vaccine were to be administered alone. Other therapies may include those known in the art, such as, e.g., analgesics, fever-reducing medications, expectorants, anti-inflammation medications, antihistamines, and/or administration of fluids.

The immunogenicity level may be determined experimentally by vaccine dose titration and challenge study techniques generally known in the art. Such techniques typically include vaccinating a number of animal subjects with the vaccine at different dosages and then challenging the animal subjects with the virulent virus to determine the minimum protective dose.

Factors affecting the preferred dosage regimen may include, for example, the breed of an equine, age, weight, sex, diet, activity, lung size, and condition of the subject; the route of administration; the efficacy, safety, and duration-of-immunity profiles of the particular vaccine used; whether a delivery system is used; and whether the vaccine is administered as part of a drug and/or vaccine combination. Thus, the dosage actually employed can vary for specific animals, and, therefore, can deviate from the typical dosages set forth above. Determining such dosage adjustments is generally within the skill of those in the art of vaccine development using conventional means.

Similarly, the volume with which such a dose can be administered typically lies between 0.1 mL (typical for intradermal or transdermal application) and 5.0 mL. A typical range for the administration volume is between 0.2 and 2.0 mL. In specific embodiments a range for the administration volume is about 1.0 to 2.0 mL for intramuscular or subcutaneous administration. In alternative specific embodiments a range for the administration volume is about 0.5 to 2.0 for intranasal administration.

It is contemplated that the vaccine may be administered to the vaccine recipient at a single time or alternatively, two or more times over days, weeks, months, or years. In some embodiments, the vaccine is administered at least two times. In certain such embodiments, for example, the vaccine is administered twice, with the second dose (e.g., a booster) being administered at least 2 weeks after the first dose. In particular embodiments, the vaccine is administered twice, with the second dose being administered no longer than 8 weeks after the first dose. In other embodiments, the second dose is administered from 1 week to 2 years after the first dose, from 1.5 weeks to 8 weeks after the first dose, or from 2 to 4 weeks after the first dose. In other embodiments, the second dose is administered about 3 weeks after the first dose. In the above embodiments, the first and subsequent dosages may vary, such as in amount and/or form. Often, however, the dosages are the same in amount and form. When only a single dose is administered, the amount of vaccine in that dose alone generally comprises a therapeutically effective amount of the vaccine. When, however, more than one dose is administered, the amounts of vaccine in those doses together may constitute a therapeutically effective amount. In addition, a vaccine may be initially administered, and then a booster may be administered from 2 to 12 weeks later, as discussed above. However, subsequent administrations of the vaccine may be made on an annual (1-year) or bi-annual (2-year) basis, regardless as to whether a booster was administered or not.

Adjuvants & Immunostimulants

An adjuvant in general is a substance that boosts the immune response of the target in a non-specific manner. Many different adjuvants are known in the art. Non-limiting examples of adjuvants that may be used in the formulation of a vaccine made with material according to the present invention include aluminum salts (e.g., alum, aluminum hydroxide, aluminum phosphate, aluminum oxide), cholesterol, monophosphoryl lipid A adjuvants, amphigen, tocophenols, monophosphenyl lipid A, muramyl dipeptide, oil emulsions, squalane, squalene, glucans, carbomers, block copolymers, Avridine lipid-amine adjuvant, heat-labile enterotoxin from E coli (recombinant or otherwise), cholera toxin, muramyl dipeptide, Freund's Complete and-Incomplete adjuvant, vitamin E, non-ionic block polymers and polyamines such as dextransulphate, CARBOPOL® [e.g., polymers of acrylic acid cross-linked with polyalkenyl ethers or divinyl glycol], pyran, saponins and saponin derivatives, block co-polymers, and adjuvants such as those identified in U.S. Pat. Nos. 4,578,269, 4,744,983, 5,254,339, which are all herein fully incorporated by reference. Non-limiting examples of peptides that can serve as adjuvants include muramyldipeptides, dimethylglycine, or tuftsin. Non-limiting examples of oils that can serve as adjuvants include mineral oils, vegetable oils, animal oils and emulsions thereof.

Vaccines made from material according to the present invention may be formulated as oil-in-water emulsions, as water-in-oil emulsions or as water-in-oil-in-water emulsions. Non-limiting examples of oil-in-water emulsions include paraffin oil-in-water emulsions, or emulsions made from one or more of squalene, block copolymers of ethylene oxide and propylene oxide, polysorbate surfactants, and/or threonyl analogs of muramyl dipeptide.

Oils used as adjuvants may be metabolizable by the subject receiving the vaccine such as vegetable or animal oils. Such oils typically consist largely of mixtures of triacylglycerols, also known as triglycerides or neutral fats. These nonpolar, water insoluble substances are fatty acid triesters of glycerol. Triacylglycerols differ according to the identity and placement of their three fatty acid residues.

Adjuvants may also consist of components that cannot be metabolized by the body of the animal subject to which the emulsion is administered. Non-metabolizable oils suitable for use in the emulsions of the present invention include alkanes, alkenes, alkynes, and their corresponding acids and alcohols, the ethers and esters thereof, and mixtures thereof. The individual compounds of the oil may be light hydrocarbon compounds, e.g., compounds having 6 to 30 carbon atoms. The oil may be synthetically prepared or purified from petroleum products. Non-limiting examples of non-metabolizable oils for use in the preparation of vaccines based upon material cultured according to the present invention include mineral oil, paraffin oil, and cycloparaffins, for example. The term "mineral oil" refers to a non-metabolizable adjuvant oil that is a mixture of liquid hydrocarbons obtained from petrolatum via a distillation technique. The term is synonymous with "liquefied paraffin," "liquid petrolatum" and "white mineral oil." The term is also intended to include "light mineral oil," i.e., oil which is similarly obtained by distillation of petrolatum, but which has a slightly lower specific gravity than white mineral oil.

Other compounds capable of enhancing a humoral immunity response that may be used in the formulation of vaccines based upon material cultured according to the present invention include, without limitation, ethylene maleic anhydrate (EMA) copolymer, latex emulsions of a copolymer of styrene with a mixture of acrylic acid and methacrylic acid.

In addition to the adjuvant, a vaccine based upon material cultured according to the present invention can include immunomodulatory agents such as, e.g., interleukins, interferons, or other cytokines [e.g., Th1-related cytokines, such as interleukin-12 (IL-12), interleukin-18 (IL-18), or gamma interferon]. The amount of adjuvant or immunostimulant added in a vaccine formulation based upon material cultured according to the present invention depends on the nature of the adjuvant or immunostimulant itself. The skilled artisan is capable of selecting an amount that is sufficient to enhance an immune response to the viral immunizing agent.

Carriers

Pharmaceutically acceptable carriers suitable for use in vaccines comprising material according to the present invention may be any conventional liquid carrier suitable for veterinary pharmaceutical compositions, including balanced salt solutions suitable for use in tissue culture media. Pharmaceutically acceptable carriers are understood to be compounds that do not adversely affect the health of the animal to be vaccinated, at least not to the extent that the adverse effect is worse than the effects seen when the animal is not vaccinated. Suitable carriers also include sterile water, saline, aqueous buffers such as PBS, solvents, diluents, isotonic agents, buffering agents, dextrose, ethanol, mannitol, sorbitol, lactose and glycerol, and the like.

Vehicle

Vaccines formulated from material according to the present invention may also comprise a vehicle. A vehicle is a compound to which the host cells, bacterial cells, or proteins, protein fragments, nucleic acids or parts thereof adhere, without being covalently bound to it. Non-limiting examples of such vehicles include bio-microcapsules, micro-alginates, liposomes, and macrosols. Some materials that serve as adjuvants can also serve as vehicles such as aluminum-hydroxide, aluminum phosphate, aluminum sulphate or aluminum oxide, silica, kaolin, and bentonite, which are all known in the art.

Stabilizers and Preservatives

Often, a vaccine is mixed with stabilizers and/or preservatives, e.g., to protect degradation-prone components from being degraded, to enhance the shelf-life of the vaccine, or to improve freeze-drying efficiency. Non-limiting examples of stabilizers that may be added to vaccine formulations based upon material cultured according to the present invention include SPGA, skimmed milk, gelatins, bovine serum albumin, carbohydrates (e.g., sorbitol, mannitol, trehalose, starch, sucrose, dextran or glucose), proteins (e.g., albumin, casein or degradation products thereof), non-animal origin stabilizers, and buffers (e.g., alkali metal phosphates). Non-limiting examples of preservatives include gentamycin (e.g., gentamycin sulfate), amphotericin, penicillin, streptomycin, EDTA, glycerol, and any combination thereof.

Freeze-Drying/Reconstitution

For reasons of stability or economy, vaccines based upon material cultured according to the present invention may be freeze-dried. In general this will enable prolonged storage at temperatures above 0° C., e.g., at 4° C. Procedures for freeze-drying are known to persons skilled in the art. Equipment for freeze-drying at different scales is available commercially. To reconstitute the freeze-dried vaccine, it may be suspended in a physiologically acceptable diluent. Such diluents may be as simple as sterile water, a physiological salt solution or other carrier as discussed above. In certain embodiments, a vaccine of the present invention can be formed into freeze-dried compositions, such as spheres, e.g., as produced by a method previously described [see e.g., WO 2010/125084; US 2012/0049412 A1, hereby incorporated by reference in their entireties].

Biological Deposit

Cultures of the following biological material have been deposited with the following international depository: American Type Culture Collection (ATCC) 10801 University Boulevard, Manassas, Va. 20110-2209, U.S.A., under conditions that satisfy the requirements of the Budapest Treaty. All restrictions imposed by the depositor on the availability to the public of the deposited material will be irrevocably removed upon granting of a patent.

| Organism | Accession No. | Date of Deposit |
|---|---|---|
| Equine Influenza Virus A/Eq/Florida/2013 (EIV FL/13 MSV Lot 9094140M01) | PTA-121715 | Nov. 11, 2014 |

EXAMPLES

Example 1

Isolation and Characterization of Two Novel EIV Isolates

Equine Influenza Virus A/Eq/Florida/2013 Isolate

The Equine Influenza Virus A/Eq/Florida/2013 [or written as FL13; A.Eq.Florida.2013; or EIV FL/13 MSV Lot 9094140M01] isolate originated from a nasal secretion sample collected from a 6 year-old Warmblood gelding. The gelding was documented as having an acute onset of mucopurulent nasal discharge and fever (103.8° F.). The sample was identified by PCR as Equine Influenza Virus (EIV). Multiple horses were affected and all of these horses had been vaccinated with EIV vaccine containing clade I and clade II EIV isolates. Samples from 39 horses were received, 13 of the 39 samples were identified as EIV by PCR.

One particular EIV isolate was passaged twice in eggs to expand. The allantoic fluid from each egg passage tested negative for bacterial contamination using TSA II+5% sheep blood agar plates. The isolate derived from the egg passage 2 was adapted to tissue culture by passaging 3 times using a canine kidney cell line. Two rounds of limiting dilution cloning (4th and 5th pass) were then conducted on the canine kidney cell line for the 3rd pass. The 2nd round limiting dilution clone harvest was used to infect the cells for the 3rd pass. This sixth passage on the canine kidney cell line was frozen down as the Pre-Master Seed.

Nucleotide and Amino Acid Sequence of HA Protein of EIV FL13 Isolates

The EIV virus in the premaster seeds of the FL13 isolates was amplified using established protocols. This allowed the HA gene to be sequenced with the use of existing primers for the HA gene. The nucleotide sequence (positive sense strain) of HA of FL13 is listed as SEQ ID NO: 3 (SEQ ID NO: 1 for the nucleotide sequence encoding only the mature HA). The deduced protein sequence (including the 15 amino acid signal peptide at N-terminus) for the HA protein of FL13 isolates is listed as SEQ ID NO: 4 (SEQ ID NO: 2 for the amino acid sequence of the mature HA).

Currently, the OIE panel for vaccine strain updates recommends that the EIV A/Ohio/2003-like isolate be employed as the representative clade 1 strain. The EIV A/Ohio/2003 (or written as OH03) isolate is a representative strain from the EIV outbreak in 2003 and as of 2013, is not included in any of the EIV vaccines presently available on the market. FIG. 1 depicts the amino acid sequence alignment of HA protein from the FL13 and OH03 EIV strains. The amino acid residue positions of the HA referred to herein follows the nomenclature of the amino acid sequence of the mature HA protein, i.e., minus the signal peptide. As can be seen in Table 1, the EIV isolate FL13 has 9 amino acid changes relative to the EIV OH03 isolate. Of these amino acid changes in the HA protein sequence, the EIV FL13 isolate comprises significant changes at seven distinct positions (amino acid residues: 7, 62, 104, 138, 188, 222, and 223). The amino acid residue changes in FL13 isolates relative to OH03 include: an aspartic acid residue at position 7 ($D_7$) in place of a glycine residue, a lysine residue at position 62 ($K_{62}$) in place of an arginine residue, an asparagine residue at position 104 ($N_{104}$) in place of an aspartic acid residue, a serine residue at position 138 ($S_{138}$) in place of an alanine residue, a threonine residue at position 188 ($T_{188}$) in place of asparagine residue, and an isoleucine residue at position 223 ($I_{223}$) in place of a valine residue. At position 222 the tryptophan residue of OH03 isolate ($W_{222}$), is replaced by a leucine residue in the FL13 isolate.

All seven of these amino acid residue changes of FL13 appear to be unique, though changes in some amino acid residues (7, 62, 104, 138, 188 and 222) had been noted in some EIV isolates from 2003 to 2012 [Lewis et al., *J. of Virol.* 85:12742-12749 (2011); Woodward et al., *Veterinary Microbiology* 169:113-127 (2014)]. However, to our knowledge, none of the published EIV sequences carry amino acid changes at position 222 together with either or both position 188 and position 223 in HA region of the amino acid sequence of SEQ ID NO: 2, as the EIV isolate, FL13, as identified herein.

Potential Structural and Functional Changes:

The influenza virus HA amino acid sequence is highly conserved in each subtype among all species. For human influenza virus subtype H3, multiple neutralizing antibodies (nAbs) targeting the HA protein have been identified and characterized. The epitopes of several neutralizing antibodies against HA have been extensively characterized by three-dimensional structural analysis of the HA protein-antibody complex. Table 2 lists the location of the amino acid residues of the epitopes for three representative neutralizing antibodies, BH151, HC45 and HC63 [Fleury et al., *Nature Structure Biology*, 6:530-534 (1999); Fleury et al., *Proteins: Structure, Function and Genetics*, 40:572-578 (2000); Barbey-Martin et al., *Virology* 294:70-74 (2002)] for human influenza virus subtype H3. The FL13 EIV isolates are also a subtype H3 influenza virus. One amino acid residue change $K_{62}$ in the FL13 EIV isolate is located in the epitopes of the neutralizing antibodies BH151 and HC45. Another amino acid residue change $T_{188}$ in the FL13 EIV isolate is located in the epitope of the neutralizing antibody HC63. In an EIV outbreak of 2003, two amino acid residues located at positions 78 and 159 in the HA protein had been shown to be responsible for the major EIV antigenic shift in 2003 [Lewis et al., *J. of Virol.* 85:12742-12749 (2011)]. Interestingly, the amino acid residues at position 78 is located in the epitope of both neutralizing antibody BH151 and HC45, and the amino acid residue at 159 is located in the epitope of neutralizing antibody HC63. These findings indicate that the epitopes of neutralizing antibodies BH151, HC45 and HC63 might be a hot spot for virus antigenic shift that evades the host immune response to EIV. Amino acid residue changes at positions 62 and 188 in FL13 isolates might contribute to the virus breakthrough of the vaccine by escaping the neutralizing antibodies generated by the vaccine strain.

The receptor binding site (RBS) is highly conserved in HA proteins among all clade I subtype H3 influenza viruses across different species. It is well documented that the following residues are involved in the receptor binding, including amino acid residues at positions 98, 135, 136, 137, 153, 183, 190, and 194 [Skehle and Wiley, *Annu Rev Biochem*, 2000, 69:531-569]. FIG. 2 shows the sequence alignment of HK68 human influenza virus (A.Human.HK.1968), equine influenza virus OH03 (A.Eq.Ohio.2003), and FL13 (A.Eq.Florida.2013). Among the amino acid residues of the RBS, $Y_{98}$, $S_{136}$, $W_{153}$, $H_{183}$ and $Q_{190}$ remain the same in all three virus isolates. Notably, the $S_{138}$ amino acid change in FL13 is very close to residues 135-137, both in the primary amino acid sequence of the RBS as well as in space, indicating that this amino acid change might contribute to the virus antigenic shift by evading some neutralizing antibody targeting at the RBS proximal region.

TABLE 1

Amino Acid Changes in the HA Protein of EIV FL13 Isolates

| AA | From (OH03) | To (FL13) | Location on the HA Trimer Structure and Potential Functional and Structual Changes |
|---|---|---|---|
| 7 | Gly | Asp | Located at the N-terminus of the HA protein. |
| 20 | Val | Ala | N/A |
| 62 | Arg | Lys | $K_{62}$ is located in the epitope of the nAbs BH151 and HC45. The $R_{62}$ to $K_{62}$ change may abolish or reduce the BH151 and HC45-like nAb binding to this region of the HA trimer. |
| 104 | Asp | Asn | $N_{104}$ is located in the inner core of the HA trimer. The $D_{104}$ to $N_{104}$ change may rearrange the structure of HA timer and affect the exposure for some nAbs. |
| 138 | Ala | Ser | $S_{138}$ is proximal to RBS. An $A_{138}$ to $S_{138}$ change may abolish or reduce the binding of an nAb targeting to this region. |
| 188 | Asn | Thr | $T_{188}$ is located in the epitope of nAb HC63. The $N_{188}$ to $T_{188}$ change may abolish or reduce the HC63-like nAb binding to this region of the HA trimer. |
| 222 | Trp | Leu | $L_{222}$ and $R_{222}$ are on the surface of the HA protein. In combination with 188 and 223, these amino acid changes might result in the structural change of HA trimeric structure, and thereby, interfere with a neutralizing antibody binding to this region. |
| 223 | Val | Ile | $I_{223}$ is located on the surface of the HA protein. In combination with 188 and 222, the amino acid changes might result in the structural change of the HA trimeric structure. |
| 311 | Gln | Arg | N/A |

*The changes at amino acid residues 20 and 311 were considered unimportant and therefore, were not further analyzed (N/A).

Example 2

Structure Modeling of Ha Protein of FL13 Isolate

Homology Model Building

The crystal structure of the HA protein from human influenza virus H3N2 (PDB 2HMG) was used as a template for the homology model building of the HA protein of EIV FL13. The overall sequence homology of the two proteins is 85%. The crystal structure contains three identical HA monomers, each consists of HA1 and HA2 subunits. HA2 is a long helical chain anchored in the membrane, and HA1 is a large globular domain. The MOE® molecular modeling software [Chemical Computing Group, Montreal, Canada] was used in this study.

The Effect of Mutations:

The amino acid changes (amino acid residues positions: 7, 62, 104, 138, 188, 222 and 223) discussed in the previous section were mapped onto the structural model of the HA protein of FL13 (FIG. 3). Except for the amino acid residue at position 7, which is located at the N-terminal tail of the HA stem close to the membrane, the rest of the mutations occur in the HA1 membrane-distal globular head at the HC45 and HC63 epitopes and the RBS (FIG. 4). Molecular modeling of these mutations indicates that these changes would affect antibody neutralization by altering the HA-antibody interactions.

R62K Mutation:

Based on the structural model, R62K is located at the center of the HC45 epitope (FIG. 5a). Superposition of the model of the EIV HA with the X-ray structure of the complex of human HA-HC45 (pdb 1QFU) shows that R62 would interact with Y32 of the HC45 neutralizing antibody (FIG. 5b). While both the arginine and lysine are capable of making cation-pi interactions with Y32, lysine is not able to make the pi-pi stacking interactions that the arginine can. Therefore, this mutation may reduce the strength of interactions with the HC45 neutralizing antibody.

N188T Mutation:

As shown in FIG. 6a, N188 is located at the HC63 epitope which partly overlaps with the RBS. It is involved in polar interactions at the HA1-HA1 interface, namely N188 of the HA1 (1) interacting with S201 and N246 of HA1 (2) (FIG. 6b). The N188T mutation would replace the strong polar functionality of asparagine with the weak polar capability of threonine. Therefore N188T would interrupt this network of stabilizing interactions and would be expected to have a detrimental effect on antigen-antibody binding.

A138S and (W222L+V223I) Mutations:

The A138S and (W222L+V223I) mutations occur around the RBS region. As shown in FIG. 7a, A138S is next to G137 at the perimeter of the RBS, and additionally makes direct contact with Y98 (the closest heavy atom distance 4.0 Å). Both proximities may affect the conformation of the binding site. A138S also could introduce a polar —OH to the binding interactions. All three mutations (A138S, W222L, and V223I) cluster around Y98 which is a key residue of the RBS (FIG. 7b). A138S in combination with W222L and V223I could change the packing interactions in the region.

TABLE 2

EPITOPES OF NEUTRALIZING ANTIBODIES (nAbs) TO HA

| Neutralizing Antibody (nAb) | Amino acid Location in the Epitope of nAb | PDB code for 3D structure of nAb and HA complex | Reference |
| --- | --- | --- | --- |
| BH151[#] | 60, 62, 63, 75, 78, 79, 90, 271 | 1EO8 | Fleury et al., *Proteins: Structure, Function and Genetics*, 40:572-578 (2000) |
| HC45[#] | 60, 62, 63, 75, 78, 79, 90, 271 | 1QFU | Fleury et al., *Nature Structure Biology*, 6:530-534 (1999) |
| HC63 | 136, 137, 153, 158, 159, 186-194 | 1KEN | Barbey-Martin et al., *Virology*, 294:70-74 (2002) |

[#]Neutralizing antibodies BH151 and HC45 overlap with each other, and possess the same epitope.

SEQUENCE LISTING TABLE FOR HA

| SEQ ID NO: | Strain | Form | NA | AA |
| --- | --- | --- | --- | --- |
| 1 | FL13 | Mature | √ | |
| 2 | FL13 | Mature | | √ |
| 3 | FL13 | Uncleaved | √ | |
| 4 | FL13 | Uncleaved | | √ |
| 5 | Ohio 03 | Mature | √ | |
| 6 | Ohio 03 | Mature | | √ |
| 7 | Ohio 03 | Uncleaved | √ | |
| 8 | Ohio 03 | Uncleaved | | √ |

The Nucleotide Sequence that Encodes the HA Protein of FL13 EIV Isolate (SEQ ID NO: 3):

The nucleotide sequence that encodes the mature HA protein begins at position 46 (SEQ ID NO: 1). The nucleic acid sequence (1-45) encoding the signal peptide is in bold and underlined. The nucleotide sequence provided does not include the coding region for the last seventeen C-terminal amino acid residues of the HA protein. These seventeen amino acid residues are part of a highly conserved C-terminal cytoplasmic "tail" which enters the host cytoplasm. Accordingly, this portion of the HA protein is not available as an antigenic target for an infected host cell.

ATGAAGACAA CCATTATTTT GATACTACTG ACCCATTGGG

CTTACAGTCA AAACCCAATC AGTGACAACA ACACAGCCAC

ATTGTGTCTA GGACACCATG CAGCAGCAAA TGGAACATTG

GTAAAAACAA TAAGTGATGA TCAAATTGAG GTGACAAATG

CTACAGAATT AGTTCAGAGC ATTTCAATGG GGAAAATATG

CAACAATTCA TATAGAATTC TAGATGGAAA GAATTGCACA

TTAATAGATG CAATGCTAGG AGACCCCCAC TGTGACGCCT

TTCAGTATGA GAATTGGGAC CTCTTTATAG AAAGAAGCAG

CGCCTTCAGC AATTGCTACC CATATGACAT CCCTAACTAT

GCATCGCTCC GATCCATTGT AGCATCCTCA GGAACATTGG

AATTCACAGC AGAGGGATTC ACATGGACAG GTGTCACTCA

AAACGGAAGA AGTGGATCCT GCAAAAGGGG ATCAGCCGAT

AGTTTCTTTA GCCGACTGAA TTGGCTAACA AAATCCGGAA

GCTCTTACCC CACATTGAAT GTGACAATGC CTAACAATAA

AAATTTCGAC AAGCTATACA TCTGGGGGAT CCATCACCCG

AGCTCAACTC AAGAGCAGAC AAAATTGTAC ATCCAAGAAT

CAGGGCGAGT AACAGTCTCA ACAAAAAGAA GTCAACAAAC

AATAATCCCT AACATCGGGT CTAGACCATT GATCAGAGGT

CAATCAGGTA GGATAAGCAT ATACTGGACC ATTGTAAAAC

CTGGAGATAT CCTAATGATA AACAGTAATG GCAACTTAGT

TGCACCGAGG GGATATTTTA AATTGAAAAC AGGGAAAAGC

TCTGTAATGA GATCAGATGT ACCCATAGAC ATTTGTGTGT

CTGAATGTAT TACACCAAAT GGAAGCATCT CCAACGACAA

GCCATTCCAA AATGTGAACA AAGTTACATA TGGAAAATGT

CCCAAGTATA TCAGACGAAA CACTTTAAAG CTGGCCACTG

GGATGAGGAA TGTACCAGAA AAGCAAATCA GAGGAATCTT

TGGGGCAATA GCGGGATTCA TCGAAAACGG CTGGGAAGGA

```
ATGGTTGATG GATGGTATGG GTTCCGATAC CAAAACTCTG

AAGGAACAGG GCAAGCTGCA GATCTAAAGA GCACTCAAGC

AGCCATCGAC CAGATCAATG GAAAGTTAAA CAGAGTGATT

GAAAGAACCA ATGAGAAATT CCATCAAATA GAGAAGGAAT

TCTCAGAAGT AGAAGGAAGA ATTCAGGACT GGAGAAATA

TGTAGAAGAC ACCAAAATAG ACCTATGGTC CTACAATGCA

GAATTGCTGG TGGCTCTAGA AAATCAACAT ACAATTGACT

TAACAGATGC AGAAATGAAC AAATTATTTG AGAAGACTAG

ACGCCAGTTA AGAGAAAACG CAGAAGACAT GGGAGGTGGA

TGTTTCAAGA TTTACCACAA ATGTGATAAT GCATGCATTG

GATCAATAAG AAATGGGACA TATGACCATT ACATATACAG

AGATGAAGCA TTAAACAACC GATTTCAGAT CAAAGGTGTA

GAGTTGAAAT CAGGCTACAA AGATTGGATA CTGTGGATTT

CATTCGCCAT ATCATGCTTC TTAATTTGCG TTGTTCTATT

GGGTTT
```

The Amino Acid Sequence of the HA Protein of FL13 EIV Isolate (SEQ ID NO: 4):
The mature HA protein begins at position 16 (SEQ ID NO: 2); the signal peptide at the N-terminal (residue 1-15) is highlighted by bold font with underline, this signal peptide will be cleaved from the mature HA protein. The amino acid sequence provided does not include the last seventeen C-terminal amino acid residues of the HA protein. These seventeen amino acid residues are part of a highly conserved C-terminal cytoplasmic "tail" which enters the host cytoplasm. Accordingly, this portion of the HA protein is not available as an antigenic target for an infected host cell.

```
MKTTIILILL THWAYSQNPI SDNNTATLCL GHHAAANGTL

VKTISDDQIE VTNATELVQS ISMGKICNNS YRILDGKNCT

LIDAMLGDPH CDAFQYENWD LFIERSSAFS NCYPYDIPNY

ASLRSIVASS GTLEFTAEGF TWTGVTQNGR SGSCKRGSAD

SFFSRLNWLT KSGSSYPTLN VTMPNNKNFD KLYIWGIHHP

SSTQEQTKLY IQESGRVTVS TKRSQQTIIP NIGSRPLIRG

QSGRISIYWT IVKPGDILMI NSNGNLVAPR GYFKLKTGKS

SVMRSDVPID ICVSECITPN GSISNDKPFQ NVNKVTYGKC

PKYIRRNTLK LATGMRNVPE KQIRGIFGAI AGFIENGWEG

MVDGWYGFRY QNSEGTGQAA DLKSTQAAID QINGKLNRVI

ERTNEKFHQI EKEFSEVEGR IQDLEKYVED TKIDLWSYNA

ELLVALENQH TIDLTDAEMN KLFEKTRRQL RENAEDMGGG

CFKIYHKCDN ACIGSIRNGT YDHYIYRDEA LNNRFQIKGV

ELKSGYKDWI LWISFAISCF LICVVLLG
```

The Nucleotide Sequence that Encodes the HA Protein of the OH03 EIV Isolate (SEQ ID NO: 7):
The nucleotide sequence that encodes the mature HA protein begins at position 46 (SEQ ID NO: 5). The nucleotide sequence (1-45) encoding the signal peptide is in bold and underlined.

```
ATGAAGACAA CCATTATTTT GATACTACTG ACCCATTGGG

CTTACAGTCA AAACCCAATC AGTGGCAACA ACACAGCCAC

ATTGTGTCTG GGACACCATG CAGTAGCAAA TGGAACATTG

GTAAAAACAA TAAGTGATGA TCAAATTGAG GTGACAAATG

CTACAGAATT AGTTCAGAGC ATTTCAATGG GGAAAATATG

CAACAACTCA TATAGAATTC TAGATGGAAG AAATTGCACA

TTAATAGATG CAATGCTAGG AGACCCCCAC TGTGACGCCT

TTCAGTATGA GAATTGGGAC CTCTTTATAG AAAGAAGCAG

CGCTTTCAGC AATTGCTACC CATATGACAT CCCTGACTAT

GCATCGCTCC GATCCATTGT AGCATCCTCA GGAACATTGG

AATTCACAGC AGAGGGATTC ACATGGACAG GTGTCACTCA

AAACGGAAGA AGTGGAGCCT GCAAAAGGGG ATCAGCCGAT

AGTTTCTTTAG CCGACTGAA TTGGCTAACA AAATCTGGAA

GCTCTTACCC CACATTGAAT GTGACAATGC CTAACAATAA

AAATTTCGAC AAGCTATACA TCTGGGGGAT TCATCACCCG

AGCTCAAATC AAGAGCAGAC AAAATTGTAC ATCCAAGAAT

CAGGACGAGT AACAGTCTCA ACAAAAAGAA GTCAACAAAC

AATAATCCCT AACATCGGAT CTAGACCGTG GGTCAGAGGT

CAATCAGGCA GGATAAGCAT ATACTGGACC ATTGTAAAAC

CTGGAGATAT CCTAATGATA AACAGTAATG GCAACTTAGT

TGCACCGCGG GGATATTTTA AATTGAAAAC AGGGAAAAGC

TCTGTAATGA GATCAGATGT ACCCATAGAC ATTTGTGTGT

CTGAATGTAT TACACCAAAT GGAAGCATCT CCAACGACAA

GCCATTCCAA AATGTGAACA AAGTTACATA TGGAAAATGC

CCCAAGTATA TCAGGCAAAA CACTTTAAAA CTGGCCACTG

GGATGAGGAA TGTACCAGAA AAGCAAATCA GAGGAATCTT

TGGAGCAATA GCGGGATTCA TCGAAAACGG CTGGGAAGGA

ATGGTTGATG GGTGGTATGG GTTCCGATAT CAAAACTCTG

AAGGAACAGG GCAAGCTGCA GATCTAAAGA GCACTCAAGC

AGCCATCGAC CAGATTAATG GAAAGTTAAA CAGAGTGATC

GAAAGAACCA ATGAGAAATT CCATCAAATA GAGAAGGAAT

TCTCAGAAGT AGAAGGAAGA ATTCAGGACT GGAGAAATA

TGTAGAAGAC ACCAAAATAG ACCTATGGTC CTACAATGCA

GAATTGCTGG TGGCTCTGGA AAATCAACAT ACAATTGACT

TAACAGATGC AGAAATGAAT AAATTATTTG AGAAGACTAG

ACGCCAGTTA AGAGAAAACG CAGAAGACAT GGGAGGTGGA

TGTTTCAAGA TTTACCACAA ATGTGATAAT GCATGCATTG

GATCAATAAG AAATGGGACA TATGACCATT ACATATACAG

AGATGAAGCA TTAAACAACC GATTTCAGAT CAAAGGTGTA

GAGTTGAAAT CAGGCTACAA AGATTGGATA CTGTGGATTT

CATTCGCCAT ATCATGCTTC TTAATTTGCG TTGTTCTATT
```

```
GGGTTTCATT ATGTGGGCTT GCCAAAAAGG CAACATCAGA

TGCAACATTT GCATT
```

The Amino Acid Sequence of the HA Protein of the OH03 EIV Isolate (SEQ ID NO: 8):
The mature HA protein begins at position 16 (SEQ ID NO: 6); the signal peptide at the N-terminal (residue 1-15) is highlighted by bold font with underline. This signal peptide will be cleaved from the mature HA protein.

```
MKTTIILILL THWAYSQNPI SGNNTATLCL GHHAVANGTL

VKTISDDQIE VTNATELVQS ISMGKICNNS YRILDGRNCT

LIDAMLGDPH CDAFQYENWD LFIERSSAFS NCYPYDIPDY

ASLRSIVASS GTLEFTAEGF TWTGVTQNGR SGACKRGSAD

SFFSRLNWLT KSGSSYPTLN VTMPNNKNFD KLYIWGIHHP

SSNQEQTKLY IQESGRVTVS TKRSQQTIIP NIGSRPWVRG

QSGRISIYWT IVKPGDILMI NSNGNLVAPR GYFKLKTGKS

SVMRSDVPID ICVSECITPN GSISNDKPFQ NVNKVTYGKC

PKYIRQNTLK LATGMRNVPE KQIRGIFGAI AGFIENGWEG

MVDGWYGFRY QNSEGTGQAA DLKSTQAAID QINGKLNRVI

ERTNEKFHQI EKEFSEVEGR IQDLEKYVED TKIDLWSYNA

ELLVALENQH TIDLTDAEMN KLFEKTRRQL RENAEDMGGG

CFKIYHKCDN ACIGSIRNGT YDHYIYRDEA LNNRFQIKGV

ELKSGYKDWI LWISFAISCF LICVVLLGFI MWACQKGNIR

CNICI
```

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

It is further to be understood that all base sizes or amino acid sizes, and all molecular weight or molecular mass values, given for nucleic acids or polypeptides are approximate, and are provided for description.

What is claimed is:

1. An isolated equine influenza virus (EIV) isolate comprising a genome that encodes a hemagglutinin protein (HA) comprising an amino acid sequence that comprises 95% or greater identity with the amino acid sequence of SEQ ID NO: 2; wherein the amino acid sequence of the HA:
   comprises an amino acid residue at position 222 other than that of a tryptophan or an arginine, and either an amino acid residue at position 223 other than that of a valine, or an amino acid residue at position 188 other than that of an asparagine; or
   comprises an amino acid residue at position 222 other than that of a tryptophan or an arginine, an amino acid residue at position 223 other than that of a valine, and an amino acid residue at position 188 other than that of an asparagine;
   wherein said EIV has been inactivated through being killed in an unnatural manner.

2. The isolated EIV of claim 1, wherein said HA further comprises:
   an amino acid residue other than that of an arginine at position 62; or
   an amino acid residue other than that of an aspartic acid at position 104; or
   an amino acid residue other than that of an alanine at position 138; or
   an amino acid residue other than that of a glycine at position 7; or
   any combination thereof.

3. The isolated EIV of claim 1, wherein the amino acid residue at position 222 is that of a leucine.

4. The isolated EIV of claim 3, wherein
   the amino acid residue at position 223 is that of an isoleucine, or the amino acid residue at position 188 is that of a threonine; or
   the amino acid residue at position 223 is that of an isoleucine and the amino acid residue at position 188 is that of a threonine.

5. The isolated EIV of claim 4, wherein
   the amino acid residue at position 62 is that of a lysine; or
   the amino acid residue at position 104 is that of an asparagine; or
   the amino acid residue at position 138 is that of a serine; or
   the amino acid residue at position 7 is that of an aspartic acid; or
   any combination thereof.

6. An isolated equine influenza virus (EIV) isolate comprising the identifying characteristics of ATCC accession No. PTA-121715; wherein said EIV has been inactivated through being killed in an unnatural manner.

7. The inactivated EIV of claim 1, wherein the unnatural manner is selected from the group consisting of treatment with a synthetic agent and heating to 60-80° C. for at least 30 to 60 min.

8. The inactivated EIV of claim 7, wherein the synthetic agent is selected from the group consisting of binary ethylamine, formalin, and beta propiolactone.

9. A vaccine comprising one or more inactivated EIV of claim 1 and a pharmaceutically acceptable carrier.

10. The vaccine of claim 9, further comprising an adjuvant.

11. The vaccine of claim 9, that further comprises a clade 2 EIV.

12. The vaccine of claim 11, wherein the clade 2 EIV is selected from the group consisting of an inactivated Equine Influenza Virus/Eq/Richmond/1/2007, an inactivated A/Shropshire/1/10, an inactivated East Renfrewshire/2/11, an inactivated Northamptonshire/1/13, and any combination thereof.

13. The vaccine of claim 11, that is a multivalent vaccine that further comprises an antigen from a pathogen selected from the group consisting of an Equine Herpesvirus, an Equine Rhinitis virus, an Equine Arteritis virus, an Equine Rotavirus, a *Neorickettsia risticii* (*N. risticii*), an Equine Rotavirus, a Hendra virus, an Eastern Encephalomyelitis, a Western Encephalomyelitis, a Venezuelan Encephalomyelitis, a Japanese Encephalomyelitis, an Equine Infectious Anemia virus, a *Corynebacterium pseudotuberculosis*, a *Clostridium tetanus*, a rabies virus, a West Nile virus, a *Rhodococcus equi*, a *Streptococcus equi*, and any combination thereof.

14. A method of immunizing an equine against EIV comprising administering the vaccine of claim 13, to an equine.

15. An isolated or recombinant polypeptide comprising an amino acid sequence that comprises 95% or greater identity with the amino acid sequence of SEQ ID NO: 2; wherein the amino acid sequence of the HA:
- comprises an amino acid residue at position 222 other than that of a tryptophan or an arginine, and either an amino acid residue at position 223 other than that of a valine, or an amino acid residue at position 188 other than that of an asparagine; or
- comprises an amino acid residue at position 222 other than that of a tryptophan or an arginine, an amino acid residue at position 223 other than that of a valine, and an amino acid residue at position 188 other than that of an asparagine.

16. An immunogenic composition comprising the isolated or recombinant polypeptide of claim 15, and a pharmaceutically acceptable carrier.

17. A recombinant nucleic acid that encodes the polypeptide of claim 15.

18. A recombinant expression vector that comprises a heterologous sequence encoding the recombinant nucleic acid of claim 17.

19. A vaccine comprising the inactivated EIV of claim 4, and an inactivated Equine Influenza Virus/Eq/Richmond/1/2007.

20. A method of immunizing an equine against EIV comprising administering the vaccine of claim 19 to an equine.

* * * * *

SEQUENCE LISTING

<160> NUMBER OF SEQ ID NOS: 8

<210> SEQ ID NO 1
<211> LENGTH: 1601
<212> TYPE: DNA
<213> ORGANISM: Equine influenza virus

<400> SEQUENCE: 1

```
agtcaaaacc caatcagtga caacaacaca gccacattgt gtctaggaca ccatgcagca      60
gcaaatggaa cattggtaaa aacaataagt gatgatcaaa ttgaggtgac aaatgctaca     120
gaattagttc agagcatttc aatggggaaa atatgcaaca attcatatag aattctagat     180
ggaaagaatt gcacattaat agatgcaatg ctaggagacc cccactgtga cgcctttcag     240
tatgagaatt gggacctctt tatagaaaga agcagcgcct tcagcaattg ctacccatat     300
gacatcccta actatgcatc gctccgatcc attgtagcat cctcaggaac attggaattc     360
acagcagagg gattcacatg gacaggtgtc actcaaaacg gaagaagtgg atcctgcaaa     420 agggatcag ccgatagttt cttttagccga ctgaattggc taacaaaatc cggaagctct     480
taccccacat tgaatgtgac aatgcctaac aataaaaatt tcgacaagct atacatctgg     540
gggatccatc acccgagctc aactcaagag cagacaaaat tgtacatcca agaatcaggg     600
cgagtaacag tctcaacaaa aagaagtcaa caaacaataa tccctaacat cgggtctaga     660
ccattgatca gaggtcaatc aggtaggata agcatatact ggaccattgt aaaacctgga     720
gatatcctaa tgataaacag taatggcaac ttagttgcac cgaggggata tttttaaattg     780 aaaacaggga aaagctctgt aatgagatca gatgtaccca tagacatttg tgtgtctgaa     840
tgtattacac caaatggaag catctccaac gacaagccat tccaaaatgt gaacaaagtt     900
acatatggaa aatgtcccaa gtatatcaga cgaaacactt taaagctggc cactgggatg     960
aggaatgtac cagaaaagca aatcagagga atctttgggg caatagcggg attcatcgaa    1020
aacggctggg aaggaatggt tgatggatgg tatgggttcc gataccaaaa ctctgaagga    1080
acagggcaag ctgcagatct aaagagcact caagcagcca tcgaccagat caatggaaag    1140
```

```
ttaaacagag tgattgaaag aaccaatgag aaattccatc aaatagagaa ggaattctca   1200
gaagtagaag gaagaattca ggacttggag aaatatgtag aagacaccaa aatagaccta   1260
tggtcctaca atgcagaatt gctggtggct ctagaaaatc aacatacaat tgacttaaca   1320
gatgcagaaa tgaacaaatt atttgagaag actagacgcc agttaagaga aaacgcagaa   1380
gacatgggag gtggatgttt caagatttac cacaaatgtg ataatgcatg cattggatca   1440
ataagaaatg ggacatatga ccattacata tacagagatg aagcattaaa caaccgattt   1500
cagatcaaag gtgtagagtt gaaatcaggc tacaaagatt ggatactgtg gatttcattc   1560
gccatatcat gcttcttaat ttgcgttgtt ctattgggtt t                        1601

<210> SEQ ID NO 2
<211> LENGTH: 533
<212> TYPE: PRT
<213> ORGANISM: Equine influenza virus

<400> SEQUENCE: 2

Ser Gln Asn Pro Ile Ser Asp Asn Asn Thr Ala Thr Leu Cys Leu Gly
1               5                   10                  15

His His Ala Ala Ala Asn Gly Thr Leu Val Lys Thr Ile Ser Asp Asp
            20                  25                  30

Gln Ile Glu Val Thr Asn Ala Thr Glu Leu Val Gln Ser Ile Ser Met
        35                  40                  45

Gly Lys Ile Cys Asn Asn Ser Tyr Arg Ile Leu Asp Gly Lys Asn Cys
    50                  55                  60

Thr Leu Ile Asp Ala Met Leu Gly Asp Pro His Cys Asp Ala Phe Gln
65                  70                  75                  80

Tyr Glu Asn Trp Asp Leu Phe Ile Glu Arg Ser Ser Ala Phe Ser Asn
                85                  90                  95

Cys Tyr Pro Tyr Asp Ile Pro Asn Tyr Ala Ser Leu Arg Ser Ile Val
            100                 105                 110

Ala Ser Ser Gly Thr Leu Glu Phe Thr Ala Glu Gly Phe Thr Trp Thr
        115                 120                 125

Gly Val Thr Gln Asn Gly Arg Ser Gly Ser Cys Lys Arg Gly Ser Ala
    130                 135                 140

Asp Ser Phe Phe Ser Arg Leu Asn Trp Leu Thr Lys Ser Gly Ser Ser
145                 150                 155                 160

Tyr Pro Thr Leu Asn Val Thr Met Pro Asn Asn Lys Asn Phe Asp Lys
                165                 170                 175

Leu Tyr Ile Trp Gly Ile His His Pro Ser Ser Thr Gln Glu Gln Thr
            180                 185                 190

Lys Leu Tyr Ile Gln Glu Ser Gly Arg Val Thr Val Ser Thr Lys Arg
        195                 200                 205

Ser Gln Gln Thr Ile Ile Pro Asn Ile Gly Ser Arg Pro Leu Ile Arg
    210                 215                 220

Gly Gln Ser Gly Arg Ile Ser Ile Tyr Trp Thr Ile Val Lys Pro Gly
225                 230                 235                 240

Asp Ile Leu Met Ile Asn Ser Asn Gly Asn Leu Val Ala Pro Arg Gly
                245                 250                 255

Tyr Phe Lys Leu Lys Thr Gly Lys Ser Ser Val Met Arg Ser Asp Val
            260                 265                 270

Pro Ile Asp Ile Cys Val Ser Glu Cys Ile Thr Pro Asn Gly Ser Ile
        275                 280                 285
```

-continued

```
Ser Asn Asp Lys Pro Phe Gln Asn Val Asn Lys Val Thr Tyr Gly Lys
    290                 295                 300

Cys Pro Lys Tyr Ile Arg Arg Asn Thr Leu Lys Leu Ala Thr Gly Met
305                 310                 315                 320

Arg Asn Val Pro Glu Lys Gln Ile Arg Gly Ile Phe Gly Ala Ile Ala
                325                 330                 335

Gly Phe Ile Glu Asn Gly Trp Glu Gly Met Val Asp Gly Trp Tyr Gly
            340                 345                 350

Phe Arg Tyr Gln Asn Ser Glu Gly Thr Gly Gln Ala Ala Asp Leu Lys
        355                 360                 365

Ser Thr Gln Ala Ala Ile Asp Gln Ile Asn Gly Lys Leu Asn Arg Val
    370                 375                 380

Ile Glu Arg Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415

Lys Ile Asp Leu Trp Ser Tyr Asn Ala Glu Leu Leu Val Ala Leu Glu
            420                 425                 430

Asn Gln His Thr Ile Asp Leu Thr Asp Ala Glu Met Asn Lys Leu Phe
        435                 440                 445

Glu Lys Thr Arg Arg Gln Leu Arg Glu Asn Ala Glu Asp Met Gly Gly
    450                 455                 460

Gly Cys Phe Lys Ile Tyr His Lys Cys Asp Asn Ala Cys Ile Gly Ser
465                 470                 475                 480

Ile Arg Asn Gly Thr Tyr Asp His Tyr Ile Tyr Arg Asp Glu Ala Leu
                485                 490                 495

Asn Asn Arg Phe Gln Ile Lys Gly Val Glu Leu Lys Ser Gly Tyr Lys
            500                 505                 510

Asp Trp Ile Leu Trp Ile Ser Phe Ala Ile Ser Cys Phe Leu Ile Cys
        515                 520                 525

Val Val Leu Leu Gly
    530
```

<210> SEQ ID NO 3
<211> LENGTH: 1646
<212> TYPE: DNA
<213> ORGANISM: Equine influenza virus

<400> SEQUENCE: 3

```
atgaagacaa ccattatttt gatactactg acccattggg cttacagtca aaacccaatc     60
agtgacaaca acacagccac attgtgtcta ggacaccatg cagcagcaaa tggaacattg    120
gtaaaaacaa taagtgatga tcaaattgag gtgacaaatg ctacagaatt agttcagagc    180
atttcaatgg ggaaaatatg caacaattca tatagaattc tagatggaaa gaattgcaca    240
ttaatagatg caatgctagg agacccccac tgtgacgcct ttcagtatga gaattgggac    300
ctctttatag aaagaagcag cgccttcagc aattgctacc catatgacat ccctaactat    360
gcatcgctcc gatccattgt agcatcctca ggaacattgg aattcacagc agagggattc    420
acatggacag gtgtcactca aaacggaaga agtggatcct gcaaaagggg atcagccgat    480
agtttcttta gccgactgaa ttggctaaca aaatccggaa gctcttaccc cacattgaat    540
gtgacaatgc ctaacaataa aaatttcgac aagctataca tctgggggat ccatcacccg    600
agctcaactc aagagcagac aaaattgtac atccaagaat cagggcgagt aacagtctca    660
acaaaaagaa gtcaacaaac aataatccct aacatcgggt ctagaccatt gatcagaggt    720
```

```
caatcaggta ggataagcat atactggacc attgtaaaac ctggagatat cctaatgata      780
aacagtaatg gcaacttagt tgcaccgagg ggatatttta aattgaaaac agggaaaagc      840
tctgtaatga gatcagatgt acccatagac atttgtgtgt ctgaatgtat tacaccaaat     900
ggaagcatct ccaacgacaa gccattccaa aatgtgaaca agttacata tggaaaatgt      960 cccaagtata tcagacgaaa cactttaaag ctggccactg ggatgaggaa tgtaccagaa    1020
aagcaaatca gaggaatctt tggggcaata gcgggattca tcgaaaacgg ctgggaagga    1080
atggttgatg gatggtatgg gttccgatac caaaactctg aaggaacagg caagctgca     1140 gatctaaaga gcactcaagc agccatcgac cagatcaatg gaaagttaaa cagagtgatt    1200
gaaagaacca atgagaaatt ccatcaaata gagaaggaat tctcagaagt agaaggaaga    1260
attcaggact ggagaaaata tgtagaagac accaaaatag acctatggtc ctacaatgca    1320
gaattgctgg tggctctaga aaatcaacat acaattgact aacagatgc agaaatgaac     1380 aaattatttg agaagactag acgccagtta agagaaaacg cagaagacat gggaggtgga    1440
tgtttcaaga tttaccacaa atgtgataat gcatgcattg gatcaataag aaatgggaca    1500
tatgaccatt acatatacag agatgaagca ttaaacaacc gatttcagat caaaggtgta    1560
gagttgaaat caggctacaa agattggata ctgtggattt cattcgccat atcatgcttc    1620
ttaatttgcg ttgttctatt gggttt                                         1646

<210> SEQ ID NO 4
<211> LENGTH: 548
<212> TYPE: PRT
<213> ORGANISM: Equine influenza virus

<400> SEQUENCE: 4

Met Lys Thr Thr Ile Ile Leu Ile Leu Leu Thr His Trp Ala Tyr Ser
1               5                   10                  15

Gln Asn Pro Ile Ser Asp Asn Asn Thr Ala Thr Leu Cys Leu Gly His
            20                  25                  30

His Ala Ala Ala Asn Gly Thr Leu Val Lys Thr Ile Ser Asp Asp Gln
        35                  40                  45

Ile Glu Val Thr Asn Ala Thr Glu Leu Val Gln Ser Ile Ser Met Gly
    50                  55                  60

Lys Ile Cys Asn Asn Ser Tyr Arg Ile Leu Asp Gly Lys Asn Cys Thr
65                  70                  75                  80

Leu Ile Asp Ala Met Leu Gly Asp Pro His Cys Asp Ala Phe Gln Tyr
                85                  90                  95

Glu Asn Trp Asp Leu Phe Ile Glu Arg Ser Ser Ala Phe Ser Asn Cys
            100                 105                 110

Tyr Pro Tyr Asp Ile Pro Asn Tyr Ala Ser Leu Arg Ser Ile Val Ala
        115                 120                 125

Ser Ser Gly Thr Leu Glu Phe Thr Ala Glu Gly Phe Thr Trp Thr Gly
    130                 135                 140

Val Thr Gln Asn Gly Arg Ser Gly Ser Cys Lys Arg Gly Ser Ala Asp
145                 150                 155                 160

Ser Phe Phe Ser Arg Leu Asn Trp Leu Thr Lys Ser Gly Ser Ser Tyr
                165                 170                 175

Pro Thr Leu Asn Val Thr Met Pro Asn Asn Lys Asn Phe Asp Lys Leu
            180                 185                 190

Tyr Ile Trp Gly Ile His His Pro Ser Ser Thr Gln Glu Gln Thr Lys
        195                 200                 205
```

```
Leu Tyr Ile Gln Glu Ser Gly Arg Val Thr Val Ser Thr Lys Arg Ser
    210                 215                 220

Gln Gln Thr Ile Ile Pro Asn Ile Gly Ser Arg Pro Leu Ile Arg Gly
225                 230                 235                 240

Gln Ser Gly Arg Ile Ser Ile Tyr Trp Thr Ile Val Lys Pro Gly Asp
                245                 250                 255

Ile Leu Met Ile Asn Ser Asn Gly Asn Leu Val Ala Pro Arg Gly Tyr
            260                 265                 270

Phe Lys Leu Lys Thr Gly Lys Ser Ser Val Met Arg Ser Asp Val Pro
        275                 280                 285

Ile Asp Ile Cys Val Ser Glu Cys Ile Thr Pro Asn Gly Ser Ile Ser
    290                 295                 300

Asn Asp Lys Pro Phe Gln Asn Val Asn Lys Val Thr Tyr Gly Lys Cys
305                 310                 315                 320

Pro Lys Tyr Ile Arg Arg Asn Thr Leu Lys Leu Ala Thr Gly Met Arg
                325                 330                 335

Asn Val Pro Glu Lys Gln Ile Arg Gly Ile Phe Gly Ala Ile Ala Gly
            340                 345                 350

Phe Ile Glu Asn Gly Trp Glu Gly Met Val Asp Gly Trp Tyr Gly Phe
        355                 360                 365

Arg Tyr Gln Asn Ser Glu Gly Thr Gly Gln Ala Ala Asp Leu Lys Ser
    370                 375                 380

Thr Gln Ala Ala Ile Asp Gln Ile Asn Gly Lys Leu Asn Arg Val Ile
385                 390                 395                 400

Glu Arg Thr Asn Glu Lys Phe His Gln Ile Glu Lys Glu Phe Ser Glu
                405                 410                 415

Val Glu Gly Arg Ile Gln Asp Leu Glu Lys Tyr Val Glu Asp Thr Lys
            420                 425                 430

Ile Asp Leu Trp Ser Tyr Asn Ala Glu Leu Leu Val Ala Leu Glu Asn
        435                 440                 445

Gln His Thr Ile Asp Leu Thr Asp Ala Glu Met Asn Lys Leu Phe Glu
    450                 455                 460

Lys Thr Arg Arg Gln Leu Arg Glu Asn Ala Glu Asp Met Gly Gly Gly
465                 470                 475                 480

Cys Phe Lys Ile Tyr His Lys Cys Asp Asn Ala Cys Ile Gly Ser Ile
                485                 490                 495

Arg Asn Gly Thr Tyr Asp His Tyr Ile Tyr Arg Asp Glu Ala Leu Asn
            500                 505                 510

Asn Arg Phe Gln Ile Lys Gly Val Glu Leu Lys Ser Gly Tyr Lys Asp
        515                 520                 525

Trp Ile Leu Trp Ile Ser Phe Ala Ile Ser Cys Phe Leu Ile Cys Val
    530                 535                 540

Val Leu Leu Gly
545

<210> SEQ ID NO 5
<211> LENGTH: 1650
<212> TYPE: DNA
<213> ORGANISM: Equine influenza virus

<400> SEQUENCE: 5
agtcaaaacc caatcagtgg caacaacaca gccacattgt gtctgggaca ccatgcagta    60
gcaaatggaa cattggtaaa aacaataagt gatgatcaaa ttgaggtgac aaatgctaca    120
```

```
gaattagttc agagcatttc aatggggaaa atatgcaaca actcatatag aattctagat        180
ggaagaaatt gcacattaat agatgcaatg ctaggagacc cccactgtga cgcctttcag        240
tatgagaatt gggacctctt tatagaaaga agcagcgctt tcagcaattg ctacccatat        300
gacatccctg actatgcatc gctccgatcc attgtagcat cctcaggaac attggaattc        360
acagcagagg gattcacatg gacaggtgtc actcaaaacg gaagaagtgg agcctgcaaa        420
aggggatcag ccgatagttt ctttagccga ctgaattggc taacaaaatc tggaagctct        480
taccccacat tgaatgtgac aatgcctaac aataaaaatt cgacaagct atacatctgg         540 gggattcatc acccgagctc aaatcaagag cagacaaaat tgtacatcca agaatcagga        600
cgagtaacag tctcaacaaa aagaagtcaa caaacaataa tccctaacat cggatctaga        660
ccgtgggtca gaggtcaatc aggcaggata agcatatact ggaccattgt aaaacctgga        720
gatatcctaa tgataaacag taatggcaac ttagttgcac cgcggggata ttttaaattg        780
aaaacaggga aaagctctgt aatgagatca gatgtaccca tagacatttg tgtgtctgaa        840
tgtattacac caaatggaag catctccaac gacaagccat tccaaaatgt gaacaaagtt        900
acatatggaa aatgccccaa gtatatcagg caaaacactt taaaactggc cactgggatg        960
aggaatgtac cagaaaagca aatcagagga atctttggag caatagcggg attcatcgaa       1020
aacggctggg aaggaatggt tgatgggtgg tatgggttcc gatatcaaaa ctctgaagga       1080
acagggcaag ctgcagatct aaagagcact caagcagcca tcgaccagat taatggaaag       1140
ttaaacagag tgatcgaaag aaccaatgag aaattccatc aaatagagaa ggaattctca       1200
gaagtagaag gaagaattca ggacttggag aaatatgtag aagacaccaa aatagaccta       1260
tggtcctaca atgcagaatt gctggtggct ctggaaaatc aacatacaat tgacttaaca       1320
gatgcagaaa tgaataaatt atttgagaag actagacgcc agttaagaga aaacgcagaa       1380
gacatgggag gtggatgttt caagatttac cacaaatgtg ataatgcatg cattggatca       1440
ataagaaatg gacatatga ccattacata tacagagatg aagcattaaa caaccgattt       1500
cagatcaaag gtgtagagtt gaaatcaggc tacaaagatt ggatactgtg gatttcattc       1560
gccatatcat gcttcttaat ttgcgttgtt ctattgggtt tcattatgtg ggcttgccaa       1620
aaaggcaaca tcagatgcaa catttgcatt                                       1650
```

<210> SEQ ID NO 6
<211> LENGTH: 550
<212> TYPE: PRT
<213> ORGANISM: Equine influenza virus

<400> SEQUENCE: 6

```
Ser Gln Asn Pro Ile Ser Gly Asn Asn Thr Ala Thr Leu Cys Leu Gly
1               5                   10                  15

His His Ala Val Ala Asn Gly Thr Leu Val Lys Thr Ile Ser Asp Asp
                20                  25                  30

Gln Ile Glu Val Thr Asn Ala Thr Glu Leu Val Gln Ser Ile Ser Met
            35                  40                  45

Gly Lys Ile Cys Asn Asn Ser Tyr Arg Ile Leu Asp Gly Arg Asn Cys
        50                  55                  60

Thr Leu Ile Asp Ala Met Leu Gly Asp Pro His Cys Asp Ala Phe Gln
65                  70                  75                  80

Tyr Glu Asn Trp Asp Leu Phe Ile Glu Arg Ser Ser Ala Phe Ser Asn
                85                  90                  95

Cys Tyr Pro Tyr Asp Ile Pro Asp Tyr Ala Ser Leu Arg Ser Ile Val
```

```
            100                 105                 110
Ala Ser Ser Gly Thr Leu Glu Phe Thr Ala Glu Gly Phe Thr Trp Thr
            115                 120                 125

Gly Val Thr Gln Asn Gly Arg Ser Gly Ala Cys Lys Arg Gly Ser Ala
            130                 135                 140

Asp Ser Phe Phe Ser Arg Leu Asn Trp Leu Thr Lys Ser Gly Ser Ser
145                 150                 155                 160

Tyr Pro Thr Leu Asn Val Thr Met Pro Asn Asn Lys Asn Phe Asp Lys
                    165                 170                 175

Leu Tyr Ile Trp Gly Ile His His Pro Ser Ser Asn Gln Glu Gln Thr
                    180                 185                 190

Lys Leu Tyr Ile Gln Glu Ser Gly Arg Val Thr Val Ser Thr Lys Arg
                195                 200                 205

Ser Gln Gln Thr Ile Ile Pro Asn Ile Gly Ser Arg Pro Trp Val Arg
            210                 215                 220

Gly Gln Ser Gly Arg Ile Ser Ile Tyr Trp Thr Ile Val Lys Pro Gly
225                 230                 235                 240

Asp Ile Leu Met Ile Asn Ser Asn Gly Asn Leu Val Ala Pro Arg Gly
                    245                 250                 255

Tyr Phe Lys Leu Lys Thr Gly Lys Ser Ser Val Met Arg Ser Asp Val
                260                 265                 270

Pro Ile Asp Ile Cys Val Ser Glu Cys Ile Thr Pro Asn Gly Ser Ile
            275                 280                 285

Ser Asn Asp Lys Pro Phe Gln Asn Val Asn Lys Val Thr Tyr Gly Lys
        290                 295                 300

Cys Pro Lys Tyr Ile Arg Gln Asn Thr Leu Lys Leu Ala Thr Gly Met
305                 310                 315                 320

Arg Asn Val Pro Glu Lys Gln Ile Arg Gly Ile Phe Gly Ala Ile Ala
                    325                 330                 335

Gly Phe Ile Glu Asn Gly Trp Glu Gly Met Val Asp Gly Trp Tyr Gly
                340                 345                 350

Phe Arg Tyr Gln Asn Ser Glu Gly Thr Gly Gln Ala Ala Asp Leu Lys
            355                 360                 365

Ser Thr Gln Ala Ala Ile Asp Gln Ile Asn Gly Lys Leu Asn Arg Val
        370                 375                 380

Ile Glu Arg Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                    405                 410                 415

Lys Ile Asp Leu Trp Ser Tyr Asn Ala Glu Leu Leu Val Ala Leu Glu
                420                 425                 430

Asn Gln His Thr Ile Asp Leu Thr Asp Ala Glu Met Asn Lys Leu Phe
            435                 440                 445

Glu Lys Thr Arg Arg Gln Leu Arg Glu Asn Ala Glu Asp Met Gly Gly
        450                 455                 460

Gly Cys Phe Lys Ile Tyr His Lys Cys Asp Asn Ala Cys Ile Gly Ser
465                 470                 475                 480

Ile Arg Asn Gly Thr Tyr Asp His Tyr Ile Tyr Arg Asp Glu Ala Leu
                    485                 490                 495

Asn Asn Arg Phe Gln Ile Lys Gly Val Glu Leu Lys Ser Gly Tyr Lys
                500                 505                 510

Asp Trp Ile Leu Trp Ile Ser Phe Ala Ile Ser Cys Phe Leu Ile Cys
            515                 520                 525
```

Val Val Leu Leu Gly Phe Ile Met Trp Ala Cys Gln Lys Gly Asn Ile
    530             535                 540

Arg Cys Asn Ile Cys Ile
545             550

<210> SEQ ID NO 7
<211> LENGTH: 1695
<212> TYPE: DNA
<213> ORGANISM: Equine influenza virus

<400> SEQUENCE: 7

```
atgaagacaa ccattatttt gatactactg acccattggg cttacagtca aacccaatc     60
agtggcaaca acacagccac attgtgtctg ggacaccatg cagtagcaaa tggaacattg    120
gtaaaaacaa taagtgatga tcaaattgag gtgacaaatg ctacagaatt agttcagagc    180
atttcaatgg ggaaaatatg caacaactca tatagaattc tagatggaag aaattgcaca    240
ttaatagatg caatgctagg agaccccac tgtgacgcct ttcagtatga aattgggac     300
ctctttatag aaagaagcag cgctttcagc aattgctacc catatgacat ccctgactat    360
gcatcgctcc gatccattgt agcatcctca ggaacattgg aattcacagc agagggattc    420
acatggacag gtgtcactca aaacggaaga agtggagcct gcaaaagggg atcagccgat    480
agtttcttta gccgactgaa ttggctaaca aaatctggaa gctcttaccc cacattgaat    540
gtgacaatgc ctaacaataa aaatttcgac aagctataca tctgggggat tcatcacccg    600
agctcaaatc aagagcagac aaaattgtac atccaagaat caggacgagt aacagtctca    660
acaaaaagaa gtcaacaaac aataatccct aacatcggat ctagaccgtg ggtcagaggt    720
caatcaggca ggataagcat atactggacc attgtaaaac ctggagatat cctaatgata    780
aacagtaatg caacttagt tgcaccgcgg ggatatttta aattgaaaac agggaaaagc    840
tctgtaatga tcagatgt acccatagac atttgtgtgt ctgaatgtat tacaccaaat    900
ggaagcatct ccaacgacaa gccattccaa aatgtgaaca agttacata tggaaaatgc    960
cccaagtata tcaggcaaaa cactttaaaa ctggccactg ggatgaggaa tgtaccagaa    1020
aagcaaatca gaggaatctt tggagcaata gcgggattca tcgaaaacgg ctgggaagga    1080
atggttgatg gtggtatgg gttccgatat caaaactctg aaggaacagg caagctgca    1140
gatctaaaga gcactcaagc agccatcgac cagattaatg aaagttaaa cagagtgatc    1200
gaaagaacca tgagaaatt ccatcaaata gagaaggaat tctcagaagt agaaggaaga    1260
attcaggact ggagaaata tgtagaagac accaaaatag acctatggtc ctacaatgca    1320
gaattgctgg tggctctgga aaatcaacat acaattgact taacagatgc agaaatgaat    1380
aaattatttg agaagactag acgccagtta agagaaacg cagaagacat gggaggtgga    1440
tgtttcaaga tttaccacaa atgtgataat gcatgcattg gatcaataag aaatgggaca    1500
tatgaccatt acatatacag agatgaagca ttaaacaacc gatttcagat caaaggtgta    1560
gagttgaaat caggctacaa agattggata ctgtggattt cattcgccat atcatgcttc    1620
ttaatttgcg ttgttctatt gggtttcatt atgtgggctt gccaaaaagg caacatcaga    1680
tgcaacattt gcatt                                                    1695
```

<210> SEQ ID NO 8
<211> LENGTH: 565
<212> TYPE: PRT
<213> ORGANISM: Equine influenza virus

```
<400> SEQUENCE: 8

Met Lys Thr Thr Ile Ile Leu Ile Leu Leu Thr His Trp Ala Tyr Ser
1               5                   10                  15

Gln Asn Pro Ile Ser Gly Asn Asn Thr Ala Thr Leu Cys Leu Gly His
                20                  25                  30

His Ala Val Ala Asn Gly Thr Leu Val Lys Thr Ile Ser Asp Asp Gln
            35                  40                  45

Ile Glu Val Thr Asn Ala Thr Glu Leu Val Gln Ser Ile Ser Met Gly
    50                  55                  60

Lys Ile Cys Asn Asn Ser Tyr Arg Ile Leu Asp Gly Arg Asn Cys Thr
65                  70                  75                  80

Leu Ile Asp Ala Met Leu Gly Asp Pro His Cys Asp Ala Phe Gln Tyr
                85                  90                  95

Glu Asn Trp Asp Leu Phe Ile Glu Arg Ser Ser Ala Phe Ser Asn Cys
                100                 105                 110

Tyr Pro Tyr Asp Ile Pro Asp Tyr Ala Ser Leu Arg Ser Ile Val Ala
            115                 120                 125

Ser Ser Gly Thr Leu Glu Phe Thr Ala Glu Gly Phe Thr Trp Thr Gly
    130                 135                 140

Val Thr Gln Asn Gly Arg Ser Gly Ala Cys Lys Arg Gly Ser Ala Asp
145                 150                 155                 160

Ser Phe Phe Ser Arg Leu Asn Trp Leu Thr Lys Ser Gly Ser Ser Tyr
                165                 170                 175

Pro Thr Leu Asn Val Thr Met Pro Asn Asn Lys Asn Phe Asp Lys Leu
            180                 185                 190

Tyr Ile Trp Gly Ile His His Pro Ser Ser Asn Gln Glu Gln Thr Lys
    195                 200                 205

Leu Tyr Ile Gln Glu Ser Gly Arg Val Thr Val Ser Thr Lys Arg Ser
    210                 215                 220

Gln Gln Thr Ile Ile Pro Asn Ile Gly Ser Arg Pro Trp Val Arg Gly
225                 230                 235                 240

Gln Ser Gly Arg Ile Ser Ile Tyr Trp Thr Ile Val Lys Pro Gly Asp
                245                 250                 255

Ile Leu Met Ile Asn Ser Asn Gly Asn Leu Val Ala Pro Arg Gly Tyr
            260                 265                 270

Phe Lys Leu Lys Thr Gly Lys Ser Ser Val Met Arg Ser Asp Val Pro
    275                 280                 285

Ile Asp Ile Cys Val Ser Glu Cys Ile Thr Pro Asn Gly Ser Ile Ser
290                 295                 300

Asn Asp Lys Pro Phe Gln Asn Val Asn Lys Val Thr Tyr Gly Lys Cys
305                 310                 315                 320

Pro Lys Tyr Ile Arg Gln Asn Thr Leu Lys Leu Ala Thr Gly Met Arg
                325                 330                 335

Asn Val Pro Glu Lys Gln Ile Arg Gly Ile Phe Gly Ala Ile Ala Gly
            340                 345                 350

Phe Ile Glu Asn Gly Trp Glu Gly Met Val Asp Gly Trp Tyr Gly Phe
    355                 360                 365

Arg Tyr Gln Asn Ser Glu Gly Thr Gly Gln Ala Ala Asp Leu Lys Ser
    370                 375                 380

Thr Gln Ala Ala Ile Asp Gln Ile Asn Gly Lys Leu Asn Arg Val Ile
385                 390                 395                 400

Glu Arg Thr Asn Glu Lys Phe His Gln Ile Glu Lys Glu Phe Ser Glu
                405                 410                 415
```

```
Val Glu Gly Arg Ile Gln Asp Leu Glu Lys Tyr Val Glu Asp Thr Lys
                420                 425                 430

Ile Asp Leu Trp Ser Tyr Asn Ala Glu Leu Leu Val Ala Leu Glu Asn
                435                 440                 445

Gln His Thr Ile Asp Leu Thr Asp Ala Glu Met Asn Lys Leu Phe Glu
            450                 455                 460

Lys Thr Arg Arg Gln Leu Arg Glu Asn Ala Glu Asp Met Gly Gly Gly
465                 470                 475                 480

Cys Phe Lys Ile Tyr His Lys Cys Asp Asn Ala Cys Ile Gly Ser Ile
                    485                 490                 495

Arg Asn Gly Thr Tyr Asp His Tyr Ile Tyr Arg Asp Glu Ala Leu Asn
                500                 505                 510

Asn Arg Phe Gln Ile Lys Gly Val Glu Leu Lys Ser Gly Tyr Lys Asp
            515                 520                 525

Trp Ile Leu Trp Ile Ser Phe Ala Ile Ser Cys Phe Leu Ile Cys Val
            530                 535                 540

Val Leu Leu Gly Phe Ile Met Trp Ala Cys Gln Lys Gly Asn Ile Arg
545                 550                 555                 560

Cys Asn Ile Cys Ile
                565
```